US008207263B2

(12) United States Patent
Popot et al.

(10) Patent No.: US 8,207,263 B2
(45) Date of Patent: Jun. 26, 2012

(54) IMMOBILIZATION OF MEMBRANE PROTEINS ONTO SUPPORTS VIA AN AMPHIPHILE

(75) Inventors: Jean-Luc Popot, Paris (FR); Delphine Charvolin, Neuilly-sur-Seine (FR); Fabrice Giusti, Sceaux (FR)

(73) Assignees: Centre National de la Recherche Scientifique (CNRS), Paris (FR); Universite Paris 7—Denis Diderot, Paris (FR)

( * ) Notice: Subject to any disclaimer, the term of this patent is extended or adjusted under 35 U.S.C. 154(b) by 180 days.

(21) Appl. No.: 12/514,656

(22) PCT Filed: Nov. 13, 2007

(86) PCT No.: PCT/EP2007/062277
§ 371 (c)(1),
(2), (4) Date: Jun. 22, 2009

(87) PCT Pub. No.: WO2008/058963
PCT Pub. Date: May 22, 2008

(65) Prior Publication Data
US 2009/0275066 A1    Nov. 5, 2009

(30) Foreign Application Priority Data

Nov. 13, 2006    (FR) ..................................... 06 09882

(51) Int. Cl.
| A61K 47/48 | (2006.01) |
| C08G 63/48 | (2006.01) |
| C08G 63/91 | (2006.01) |
| C08L 89/00 | (2006.01) |
| D21H 19/50 | (2006.01) |
| C08F 20/00 | (2006.01) |
| C08F 22/38 | (2006.01) |
| C08F 26/00 | (2006.01) |
| C08F 120/00 | (2006.01) |
| C08F 220/54 | (2006.01) |
| C08F 220/70 | (2006.01) |
| C08F 222/38 | (2006.01) |
| C08F 226/02 | (2006.01) |
| C08F 236/00 | (2006.01) |
| C12Q 1/00 | (2006.01) |

(52) U.S. Cl. ...... 525/54.1; 524/17; 526/303.1; 526/306; 526/317.1; 526/287; 435/4
(58) Field of Classification Search .................. 525/54.1; 524/17; 526/303.1, 306, 317.1, 287; 435/4
See application file for complete search history.

(56) References Cited

U.S. PATENT DOCUMENTS

| 4,193,983 | A | * | 3/1980 | Ullman et al. .................. 436/528 |
| 5,393,527 | A | * | 2/1995 | Malick et al. ................... 435/7.1 |
| 6,143,358 | A | * | 11/2000 | Singh et al. .................... 427/162 |
| 6,589,943 | B2 | * | 7/2003 | Byun et al. ..................... 514/56 |
| 6,868,343 | B1 | * | 3/2005 | Bayerl et al. ................... 702/23 |
| 2002/0028766 | A1 | * | 3/2002 | Papadimitriou ................. 514/2 |
| 2004/0010381 | A1 | * | 1/2004 | Mojtabai ........................ 702/29 |
| 2004/0096895 | A1 | * | 5/2004 | Lakey et al. .................... 435/7.1 |
| 2004/0102381 | A1 | * | 5/2004 | Ekwuribe et al. ............... 514/12 |
| 2004/0202639 | A1 | * | 10/2004 | DeGrado et al. ........... 424/78.22 |
| 2005/0079552 | A1 | * | 4/2005 | Kogi .............................. 435/7.1 |
| 2005/0123610 | A1 | * | 6/2005 | Papadimitriou ............... 424/468 |
| 2005/0171596 | A1 | * | 8/2005 | Furst et al. .................... 623/1.15 |
| 2005/0175786 | A1 | * | 8/2005 | Singh et al. ................. 427/407.1 |
| 2005/0181976 | A1 | * | 8/2005 | Ekwuribe ........................ 514/2 |
| 2006/0134177 | A1 | * | 6/2006 | Liu et al. ....................... 424/427 |
| 2006/0148756 | A1 | * | 7/2006 | Darcy et al. ..................... 514/58 |
| 2006/0224095 | A1 | * | 10/2006 | Claverie et al. ................. 602/5 |
| 2006/0269479 | A1 | * | 11/2006 | Colton et al. ................. 424/1.69 |
| 2007/0026383 | A1 | * | 2/2007 | Trubetskoy et al. .............. 435/4 |
| 2007/0122443 | A1 | * | 5/2007 | Narayanan et al. ........... 424/423 |
| 2008/0305348 | A1 | * | 12/2008 | Spedden ...................... 428/497 |
| 2009/0221805 | A1 | * | 9/2009 | Dahri-Correia et al. ....... 530/399 |

FOREIGN PATENT DOCUMENTS

WO    98/27434    6/1998

OTHER PUBLICATIONS

Cooper (Nature Reviews, vol. 1, 2002, 515-528).*
Kim et al. (JACS, 2005, 127, 9588-9592).*
Giess, F., et al., The protein-tethered lipid bilayer: a novel mimic of the biological membrane, Biophys. J., 2004;87 (5):3213-20.
Pal, P., et al., A novel immobilization method for single protein spFRER studies, Biophys. J., 2005;89(2):LII-3.
Hoffman, T. L., et al., A biosensor assay for studying ligand-membrane receptor interactions : binding of antibodies and HIV-1 Env to chemokine receptors, PNAS, 2000;97:11215-11220.
Minic, J. et al., Immobilization of native membrane-bound rhodopsin on biosensor surfaces. Biochim. Biophys. Acta, 2005;1724(3), 324-32.
Cooper, M. A., Optical biosensor in drug discovery, Nat. rev. Drug Discov., 2002;1:515-528.
Tribet, C., et al., Amphipols: polymers that keep membrane proteins soluble in aqueous solutions. Proc. Natl. Acad. Sci. USA, 1996;93:15047-15050.
Popot, J. L., et al., Amphipols: polymeric surfactants for membrane biology research. Cell. Mol. Life Sci., 2003;60: 1559-1574.
Zoonens, et al., NMR study of a membrane protein in detergent-free aqueous solution. Proc. Natl. Acad. Sci. USA, Jun. 21, 2005;102(25):8893-8898.

(Continued)

Primary Examiner — Liam Heincer
(74) Attorney, Agent, or Firm — Pepper Hamilton LLP

(57) ABSTRACT

The invention pertains to the field of membrane protein immobilization onto supports. It relates to a product comprising a support and at least one membrane protein attached to the surface thereof, characterized in that said membrane protein is attached to said support using an amphiphilic molecule with which said membrane protein is complexed. It also relates to a process for preparing such product, as well as to various applications in the fields of diagnosis, drug design and biotechnologies. It further relates to a kit, together with a functionalized amphiphilic molecule, for preparing a product according to the invention comprising a support and an amphiphilic molecule, wherein the amphiphilic molecule and the support interact through a hydrophobic bond, an ionic bond, a specific bond or a covalent bond.

14 Claims, 6 Drawing Sheets

OTHER PUBLICATIONS

Picard, M., et al., Protective and inhibitory effects of various types of amphipols on the Ca2+-ATPase from sarcoplasmic reticulum: a comparative study, Biochemistry, 2006;45:1861-1869.

Nagy, J., et al., Use of amphipathic polymers to deliver a membrane protein to lipid bilayers, FEBS Lett., 2001;501: 115-120.

Xu, Q., et al, Protein and Chemical Microar]rays: Powerful Tools for Proteomics, J. Biomed. and Biotechnology, 2003;5:257-266.

Yousaf, M. N., et al., Diels-Aldert Reaction for the Selective Imobilization of Protein to Electroactive Self-Assembled Monolayers, J. Am. Chem. Soc., 1999;121:4286-4287.

Devaraj, N. K., et al., Chemoselective Covalent Coupling of Oligonucleotide Probes to Self-Assembled Monolayers, J. Am. Chem. Soc., 2005;127:8600-8601.

Taniguchi, I., et al., A Chemoselective Approach to Grafting Biodegradable Polyesters, Macromolecules, 2005;38:216-219.

Gohon, Y., et al., Partial specific volume and solvent interactions of amphipol A8-35. Anal. Biochem., 2004;334:318-334.

Gohon, Y., et al., Well-defined nanoparticles formed by hydrophobic assembly of a short and polydisperse random terpolymer, amphipol A8-35, Langmuir 2006;22:1281-1290.

Pidgeon, C., et al., Immobilized artificial membrane chromatography: rapid purification of functional membrane proteins, Analytical Biochemistry, 1991;1:163-73.

Pocanschi, C. L., et al., Amphipatic polymers: tools to fold integral membrane proteins to their active forms, Biochemistry, Apr. 2007;45(47):13954-13961.

Liu, H., et al., Single-step purifications of rat liver aldolase using immobilized artificial membrane chromatography, Journal of Chromatography B, 1997;703:53-62.

Ong, S., et al., Immobilized artificial-membrane chromatography, Journal of Chromatography A, 1996;728:113-128.

* cited by examiner

US 8,207,263 B2

IMMOBILIZATION OF MEMBRANE PROTEINS ONTO SUPPORTS VIA AN AMPHIPHILE

CROSS-REFERENCE TO RELATED APPLICATIONS

This application is the U.S. National Stage filing under 35 U.S.C. §371 of International Application Serial. No. PCT/EP2007/062277 filed Nov. 13, 2007, which claims priority under 35 U.S.C. §119(a) to French Application Serial No. 06/09882 filed Nov. 13, 2006, each of which is incorporated herein by reference in its entirety.

FIELD OF THE INVENTION

The invention pertains to the field of membrane protein immobilization onto supports. It relates to a product comprising a support and at least one membrane protein attached to the surface thereof, characterized in that said membrane protein is attached to said support using an amphiphilic molecule with which said membrane protein is complexed. It also relates to a process for preparing such product, as well as to various applications in the fields of diagnosis, drug design and biotechnologies. It further relates to a kit, together with a functionalized amphiphilic molecule, for preparing a product according to the invention comprising a support and an amphiphilic molecule, wherein the amphiphilic molecule and the support interact through a hydrophobic bond, an ionic bond, a specific bond or a covalent bond.

BACKGROUND ART

Integral membrane proteins represent about 30% of the coding sequences of eukaryotic genomes. Their functions, and especially those of these proteins which are inserted into the cell plasma membrane and exposed to the outside environment, have such an importance that they are privileged targets in the fields of biomedical sciences and pharmacology. They are in fact thought to be the target for at least 60% of the therapeutic agents currently commercially available. Membrane proteins serve in particular as binding sites, attachment points or privileged targets for multiple interactions. These range from recognizing small ligands, such as neurotransmitters or hormones, to cell association into tissues. Membrane proteins are further most often the first target for viruses, pathogenic bacteria or parasites, or antibodies during immune defense or autoimmune diseases. They can also be involved in membrane/DNA or membrane/cytoskeleton association, in regulation or deregulation of cell division (cancers), and they are recognized by macromolecular effectors such as G proteins or kinesins.

Due to their importance in the fields of biomedical sciences and pharmacology, it is absolutely essential to provide tools for studying membrane proteins and their ligands. In particular, it is important to be able to detect ligand binding to a membrane protein of interest. In fact, a process for detecting ligand binding has several very valuable applications:

in the case where the membrane protein is derived from the membrane of a pathogenic agent, such a process may be useful to detect in a biological sample obtained from a subject the presence or absence of antibodies raised against this membrane protein, and accordingly the presence or absence of an exposition of the subject to the pathogenic agent;

in the case of a human or animal membrane receptor shown to be involved in the pathogenesis of a disease and therefore providing a therapeutic target for the treatment of such disease, such a process may be useful to screen compound libraries so as to identify agonist or antagonist compounds for this membrane receptor.

To carry out a process for detecting ligand binding to a membrane protein, it is very useful to have this membrane protein immobilized onto a support. It has been long known how to attach or immobilize soluble proteins onto supports. However, the problem is more complex for membrane proteins. In fact, membrane proteins necessarily expose highly hydrophobic surfaces that, in situ, interact with the membrane, which makes their handling difficult, particularly in that it is generally necessary to use high amounts of detergents to isolate them from the membrane and to make them soluble. Compared to cytosolic proteins, their handling and accordingly their immobilization on a support is made a lot more strenuous due to their hydrophobicity.

Different immobilization techniques have been developed to deposit membrane proteins on the surface of a support. For example, by genetically or chemically modifying the protein, a functional group can be inserted at one of the extremities of the protein polypeptide chain so as to promote protein adhesion to the surface of a functionalized support (for example, by introducing a terminal His-Tag on the protein, which will interact with a support grafted with NTA groups coordinating $Ni^{2+}$ or $Co^{2+}$ ions) (1.2).

However, such a technique relies on the possibility of genetically or chemically modifying the protein of interest, and is thus difficult or impossible to implement for a membrane protein about which little information is available. Furthermore, since genetically or chemically modifying a protein involves a number of steps this can be cumbersome and tedious. Lastly, its development should be repeated for each protein of interest and accordingly this technique cannot be used either routinely or for a large number of membrane proteins simultaneously.

In another technique, it is possible, by maintaining the protein in its original cell membrane, or by inserting it into an artificial membrane (for example, a vesicle), to promote protein adhesion onto a support grafted with hydrophobic chains via interactions between the chains and the membrane (3-5). A further technique comprises utilizing the charge properties of extra-membrane domains of the protein, or hydrophilic heads of lipids of the membrane in which the protein is inserted, to promote simple electrostatic interactions with a charged support.

However, for both these techniques, either the protein is extracted from the membrane, and it is generally absolutely necessary to work in the presence of a detergent, which makes the immobilization methods considerably more complex, both because the solution properties are altered (for example by reducing the surface tension of the solutions, which can make the spotting of the proteins at the surface of the chips inaccurate) and because the presence of detergent affects the stability of a number of membrane proteins (particularly membrane complexes), or proteins inserted into natural or synthetic membranes (lipid vesicles) are used, and the technique is thus intricate and raises a sensitivity problem: the low density of the protein of interest may decrease the signal/noise ratio of the experiment, and the presence of undesirable components in the case of natural membranes (other proteins, a large variety of natural lipids, various cofactors) may introduce an interference between the experimental signal and adverse side reactions and background noise.

As a result, it is clear that the existing immobilization (or attachment) methods of membrane proteins onto supports are unsatisfactory. There is therefore a need for a process for attaching membrane proteins on supports which overcomes the above-mentioned drawbacks, i.e. for a process having the following characteristics:

- a process for maintaining membrane proteins in a completely detergent-free water-soluble and biochemically stabilized form, thus making the method simpler and preventing membrane proteins from destabilizing,
- a universal process, applicable to any membrane protein, without any particular adjustment of the experimental method to each protein and without the need for any protein modification, which can thus be used including when the protein is not fully known or when its biochemistry and its genetics are not controlled, and
- a process for attaching membrane proteins to the surface of a support with a high density, resulting in better yields and a better sensitivity of the experimental results and accordingly a better interpretation of the data.

Amphipols are polymeric amphiphiles having a good solubility, a number of hydrophobic side chains, and molecular dimensions and flexibility so as to enable them to combine at multiple points with the hydrophobic transmembrane surface of membrane proteins (FIG. 1, references 6, 7). The principle of multi-point attachment is to guarantee that desorption kinetics is very slow, so as to make the combination between the membrane protein and the amphipol essentially irreversible.

Furthermore, it has been shown that this approach is universal, which means that all membrane proteins tested to date, i.e. more than twenty, can be maintained in solution in the form of amphipol complexes (7, 8). Furthermore, the resulting trapped proteins maintain their native structure, remain soluble in the absence of free surfactant in the solution (7-9), and their stability is at worst matched but most often improved compared to keeping in detergent solution (7, 8, 10). Lastly, when a mixture of membrane proteins is trapped by amphipols under appropriate conditions, all membrane proteins in the mixture are trapped separately (8).

Amphipols are therefore a tool for stabilizing in a solution any membrane protein, irrespective of its structure, function and/or origin. However, they have only been used to date for solubilizing membrane proteins and for engineering them in a solution, or for stabilizing them temporarily, and no study has ever been disclosed as to the possibility of further using them as intermediates mediating membrane protein attachment to a support. On the contrary, up to now, amphipols have only been used in order to provide water-soluble complexes, that can move freely in a solution, from membrane proteins naturally insoluble in aqueous media, for temporarily stabilizing such membrane proteins in lipid membrane regeneration experiments (11), or for stabilizing such biotinylated membrane proteins attached through usual biotin/avidin interaction on a solid support, with amphipol only being used to stabilize the protein and not being at all involved in the combination of the membrane protein to the solid support (8).

DESCRIPTION OF THE INVENTION

The inventors have found that it is further possible to use an amphipol complexed with a membrane protein as an intermediate for attaching this membrane protein onto a support, the binding to the support being done through the amphipol.

The use of an amphipol as an intermediate for binding to the support has numerous advantages compared with known techniques. The first major advantage is that this process is usable without any change in the method to any membrane protein, irrespective of its origin or whether information is available on this protein or not. In particular, the process is applicable even to a membrane protein the identity of which is unknown. Furthermore, the process is carried out easily, in particular as there is no need to use a detergent in the attachment step of the membrane protein/amphipol complex to the support. This process also provides the attachment of the membrane proteins at the surface of a support with a high density, thus achieving better yields and above all a better sensitivity of the binding assay results of ligands onto the immobilized membrane protein.

Lastly, the presence of amphipols complexed with membrane proteins guarantees their biochemical stabilization, thus also allowing a greater accuracy and reproducibility of the binding assay results of ligands on the immobilized membrane protein.

The process developed by the inventors thus allows to readily produce, with a high density, products comprising a support and one or more known or unknown membrane proteins of any kind, attached to the surface thereof, wherein the membrane proteins are further biochemically stabilized in an aqueous medium, thereby making it much easier to carry out binding assay experiments of ligands on immobilized membrane proteins using the product obtained.

Thus, the invention relates to a product comprising a support and at least one membrane protein attached to the surface thereof, characterized in that said membrane protein is attached to said support using an amphiphilic molecule with which said membrane protein is complexed.

The term <<amphiphilic>> relates to an organic molecule displaying both hydrophilic and hydrophobic properties mediated by different portions of the molecule. Thus, an <<amphiphilic>> molecule (also called an "amphiphile") generally comprises one or more hydrophilic groups and one or more hydrophobic groups.

In the present case, the hydrophobic groups of the amphiphilic molecule bind it to the membrane protein, the transmembrane surface of which is hydrophobic per se, and the hydrophilic groups provide solubilization of the whole amphiphilic molecule/membrane protein complex. Preferably, the amphiphilic molecule comprises a number of hydrophobic side chains, enabling it to combine at a plurality of points with the hydrophobic transmembrane surface of membrane proteins, this multiple attachment resulting in very slow desorption kinetics, which makes the combination essentially irreversible. Advantageously, the number of hydrophobic side chains is greater than 10.

Furthermore, the amphiphilic molecule preferably further comprises numerous hydrophilic groups for solubilizing the amphiphilic molecule/membrane protein complex. Advantageously, the number of hydrophilic groups is greater than 20.

Preferably, the ratio of the number of hydrophobic side chains to the number of hydrophilic groups is between 0.25 and 2.5; preferably between 0.25 and 2; between 0.25 and 1.5; between 0.25 and 1; or more preferably between 0.25 and 0.5.

Advantageously also, the amphiphilic molecules used to provide a product according to the invention have molecular dimensions and a flexibility which make it possible for them to combine at a plurality of points with the hydrophobic transmembrane surface of the proteins. Accordingly, suitable amphiphilic molecules for carrying out the present invention comprise in particular amphiphilic polymers of all kinds. In this case, the basic structure of the polymer should be substituted with various groups having hydrophilic or hydrophobic properties, or being themselves amphiphilic. Thus, an admissible amphiphilic polymer should have one or more hydrophilic side chains, as well as one or more hydrophobic or amphiphilic side chains. Preferably, the ratio of the number of hydrophobic or amphiphilic side chains to the number of hydrophilic side chains should be between 0.25 and 2.5; preferably between 0.25 and 2; between 0.25 and 1.5; between 0.25 and 1; or more preferably between 0.25 and 0.5.

Admissible amphiphilic polymers include in particular amphiphilic vinyl polymers, amphiphilic polypeptides, amphiphilic polysaccharides, and amphiphilic dendrimers. Thus, in an advantageous embodiment of a product according to the invention, the amphiphilic molecule is selected from an amphiphilic vinyl polymer, an amphiphilic polypeptide, an amphiphilic polysaccharide, or an amphiphilic dendrimer.

The term <<vinyl polymer>> relates to a polymer consisting of units of the $-(CH_2-)_n-CRaR_b-$ type, wherein $R_a$ and $R_b$ are various substituents and n is a integer ranging from at least 1. Advantageously, n is between 1 and 3, more advantageously, n=1.

In a preferred embodiment, the amphiphilic molecule is an amphiphilic vinyl polymer, i.e. a vinyl polymer with one or more substituents having a hydrophilic character and one or more others having a hydrophobic character.

Preferably, the amphiphilic molecule is a vinyl polymer of the formula (I):

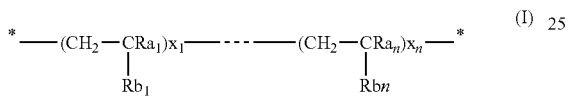

wherein:

$Ra_1$ to $Ra_n$ are the same or different, and represent a hydrogen atom, or a methyl radical:

$Rb_1$ to $Rb_n$ are different and selected from:
a hydrophilic group selected from
a carboxylate radical $-COO^-M^+$, a sulfonate radical $-SO_3^{31}\ M^+$, or a phosphonate radical $-PO_3^-M^+$, where $M^+$ is a cationic counter-ion,
a $(C_1-C_5)$ alkylcarboxylate radical, a $(C_1-C_5)$ alkylsulfonate radical, or a $(C_1-C_5)$ alkylphosphonate radical
a phenylsulfonate
CONRc1Rc2, where Rc1 and Rc2, which may be the same or different, represent a $(-C(CH_2ORd1)(CH_2ORd2)(CH_2ORd3))$ radical, where Rd1, Rd2 and Rd3 represent independently a hydrogen atom, a sugar moiety, a polyoxyalkylene, in particular polyoxyethylene, containing from 4 to 10 alkylene oxide units, a zwitterionic radical, a primary, secondary or tertiary hydroxyalkyl $-(CH_2)mOH$, where m is within the range of 1 to 4, a $(C_1-C_5)$ alkylcarboxylate radical, a $(C_1-C_5)$ alkylsulfonate radical or a $(C_1-C_5)$ alkylphosphonate radical, a sugar moiety
COORe, wherein Re represents a sugar moiety, a primary, secondary or tertiary hydroxyalkyl $-(CH_2)mOH$, where m is within the range of 1 to 4, a polyoxyalkylene, in particular polyoxyethylene, having 4 to 10 alkylene oxide units, a $(CH_2)t$-NRf1 Rf2 radical, where t is an integer from 1 to 5, and Rf1, Rf2, which may be the same or different, represent a hydrogen atom or a (C1—C4) alkyl radical,
a hydroxyl group
a primary, secondary or tertiary hydroxyalkyl $-(CH_2)mOH$, where m is within the range of 1 to 4,
a primary, secondary, tertiary amine
a quaternary ammonium
N-formamide, N-alkylformamide,
N-acetamide, N-alkylacetamide,
N-pyrrolidonyl,
CONRg1 Rg2, where Rg1 and Rg2, which may be the same or different, are a hydrogen atom, a sugar moiety, a polyoxyalkylene, in particular polyoxyethylene, containing from 4 to 10 alkylene oxide units, a zwitterionic radical, a primary, secondary or tertiary hydroxyalkyl $-(CH_2)mOH$, where m is within the range of 1 to 4,
COORh or CONRkR1, where Rh represents a $(C_1-C_5)$ alkyl radical, an alkylsulfonate, or has one of the meanings given for Re or Rg1, provided that it is not a hydrogen atom, and Rk and R1 have independently one of the meanings given for Rh, and additionally one of them can represent a hydrogen atom;
a hydrophobic group selected from:
a hydrogen atom,
a halogen atom,
a $-CONH(-C(CH_2ORm1)(CH_2ORm2)(CH_2ORm3))$ radical, wherein Rm1, Rm2, Rm3 are independently a linear or branched alkyl, alkenyl or alkynyl having from 3 to 50 carbon atoms, an alkylcarbamoyl (O=C—NH—Rn) or an acyl (O=C-Ro), where Rn and Ro are linear or branched alkyl, alkenyl or alkynyl radicals having from 3 to 50 carbon atoms,
COORp, CORp, COSRp, C—NH—Rp or CONRq1Rq2, where Rp is a linear or branched and/or cyclic alkyl, alkynyl or alkenyl radical containing from 3 to 50 carbon atoms, and Rq1 and Rq2, which may be the same or different, have one of the meanings given for Rp, and further either one of them can represent a hydrogen atom,
a —Rr, —ORr, or —SRr radical where Rr represents a linear or branched and/or cyclic alkyl, alkenyl or alkynyl group containing from 3 to 50 carbon atoms; or
an amphiphilic group selected from:
an alkyl radical $-(CH_2)m$-Rs, where m is between 6 and 20, and where Rs is a hydrophilic group such as carboxylate, sulfonate, phosphonate, sulfate, phosphate, zwitterion, ammonium, poly(oxyethylene), or sugar,
a poly(oxyethylene)—O-alkyl radical $(-(CH_2CH_2O)m$-Rt) where Rt is a linear, branched or cyclic alkyl, alkenyl, alkynyl radical with 6 to 20 carbon atoms,
a COORu, CORu, COSRu, CONRvRw radical, wherein Ru is a poly(oxyethylene)—O-alkyl radical $(-(CH_2CH_2O)m$-Rt) where Rt is a linear, branched or cyclic alkyl, alkenyl, alkynyl radical with 6 to 20 carbon atoms, a glycosylalkyl radical, wherein Rv may be a hydrogen atom or has one of the meanings given for Ru, wherein Rw has one of the meanings given for Ru,
a $-CONH(-C(CH_2ORx1)(CH_2ORx2)(CH_2ORx3))$ radical, wherein Rx1, Rx2, Rx3 are such that one or two of these groups have one of the meanings given for Rm1, Rm2, Rm3 and one or two of these groups are different from a hydrogen atom and have one of the meanings given for Rd1, Rd2, Rd3, Ru,
or Rx1, Rx2, Rx3 are the same or different, and are such that at least one of the groups is different from a hydrogen atom and has one of the meanings given for Ru,
n is an integer equal to or greater than 2, preferably between 2 and 10, between 2 and 8, between 2 and 6, between 2 and 4, advantageously n is 3;

$x_1$ to $x_n$, respectively, represent the percentages of the units $$\left(\sum_{i=1}^{n} x_i = 100\%\right),$$

where the ratio of the total percentage of groups where $Rb_i$ is a hydrophobic or amphiphilic group to the total percentage of groups where $Rb_i$ is a hydrophilic group $$\sum_{hydrophobic\ Rb_{ii}} x_i + \sum_{amphiphilic\ Rb_j} x_j \Bigg/ \sum_{hydrophilic\ Rb_k} x_k$$

is between 0.25 and 2.5; preferably between 0.25 and 2; between 0.25 and 1.5; between 0.25 and 1; or more preferably between 0.25 and 0.5; and the average molecular weight is between 500 and 100,000, advantageously between 1,000 and 50,000, between 2,000 and 25,000, more advantageously between 4,000 and 15,000, between 6,000 and 12,000, and preferably between 8,000 and 10,000, or more preferably between 9,000 and 10,000 g.mol$^{-1}$.

The term <<cationic counter-ion>> according to the invention relates to a cation which is able to neutralize the negative charge carried by the negatively charged oxygen atom of the COO$^-$ group of R1 when R1 is COO-M$^+$. This counter-ion can be in particular an alkaline cation.

The term <<sugar moiety>> according to the invention relates to a mono or hetero or homopolysaccharide radical, in particular, but not limited to, of the formula $(C_nH_{2n-2}O_{n-1})_m$. When m=1 the monosaccharide can be a glucosyl, galactosyl, mannosyl radical, and the like. When m=2 the disaccharide can be a maltosyl, lactosyl, saccharosyl radical, and the like.

The term <<polyoxyalkylene>> according to the invention relates to a radical of the formula $(C_nH_{2n}O)_m$, where n is an integer between 1 and 6 and m is an integer equal to or greater than 2. This includes in particular the polyoxyethylene where n=2.

The term <<zwitterionic radical>> according to the invention is meant to relate to, according to the invention, a group carrying both a positive charge and a negative charge such as a carboxybetaine group of the general formula —$(CH_2)_n$—N$^+$Ry1Ry2-$(CH_2)_m$—CO$_2^-$, a sulfobetaine group of the general formula —$(CH_2)_n$—N$^+$Rz1Rz2-$(CH_2)_m$—SO$_3^-$ where Ry1, Ry2 Rz1 and Rz2 are linear, branched or cyclic alkyl, alkenyl or alkyl radicals, and n is an integer equal to or greater than 1 and m is an integer within the range of 2 to 4.

The term <<alkylsulfonate>> according to the invention relates to a radical of the general formula —$(CH_2)_n$—SO$_3$-M$^+$ where M$^+$ is as defined above.

In all cases above and below referring to a linear or branched alkyl, alkenyl or alkynyl having from 3 to 50 carbon atoms, the linear or branched alkyl, alkenyl or alkynyl radical comprises advantageously from 3 to 40, from 3 to 30, from 3 to 25, from 3 to 20, or more preferably from 3 to 18 carbon atoms.

Advantageously, the vinyl polymer is more specifically of the formula (II):

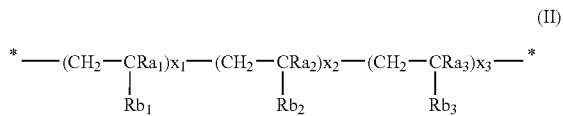

wherein:
Ra$_1$, Ra$_2$ and Ra$_3$ are the same or different, and represent a hydrogen atom, or a methyl radical;
Rb$_1$ is a hydrophilic group selected from:
  a carboxylate radical —COO$^-$M$^+$, a sulfonate radical —SO$_3^-$M$^+$, or a phosphonate radical —PO$_3^-$M$^+$, where M$^+$ is a cationic counter-ion,
  a $(C_1-C_5)$ alkylcarboxylate radical, a $(C_1-C_5)$ alkylsulfonate radical, or a $(C_1-C_5)$ alkylphosphonate radical
  a phenylsulfonate
  CONRc1Rc2, where Rc1 and Rc2, which may be the same or different, represent a (—C(CH$_2$ORd1)(CH$_2$ORd2)(CH$_2$ORd3)) radical, where Rd1, Rd2 and Rd3 represent independently a hydrogen atom, a sugar moiety, a polyoxyalkylene, in particular polyoxyethylene, containing from 4 to 10 alkylene oxide units, a zwitterionic radical, a primary, secondary or tertiary hydroxyalkyl —(CH$_2$)mOH, where m is within the range of 1 to 4, a $(C_1-C_5)$ alkylcarboxylate radical, a $(C_1-C_5)$ alkylsulfonate radical or a $(C_1-C_5)$ alkylphosphonate radical, a sugar moiety
Rb$_2$ is:
  a hydrophobic group selected from:
    a hydrogen atom,
    a halogen atom,
    a —CONH(—C(CH$_2$ORm1)(CH$_2$ORm2)(CH$_2$ORm3)) radical, wherein Rm1, Rm2, Rm3 are independently a linear or branched alkyl, alkenyl or alkynyl having from 3 to 50 carbon atoms, an alkylcarbamoyl (O═C—NH—Rn) or an acyl (O═C-Ro), where Rn and Ro are linear or branched alkyl, alkenyl or alkynyl radicals having from 3 to 50 carbon atoms,
    COORp, CORp, CSRp, C—NH-Rp or CONRq1Rq2, where Rp is a linear or branched and/or cyclic alkyl, alkynyl or alkenyl radical containing from 3 to 50 carbon atoms, and Rq1 and Rq2, which may be the same or different, have one of the meanings given for Rp, and further either one of them can represent a hydrogen atom,
    a —Rr, —ORr, or —SRr radical where Rr represents a linear or branched and/or cyclic alkyl, alkenyl or alkynyl group containing from 3 to 50 carbon atoms; or
  an amphiphilic group selected from:
    an alkyl radical —(CH$_2$)m-Rs, where m is between 6 and 20, Rs is a hydrophilic group such as carboxylate, sulfonate, phosphonate, sulfate, phosphate, zwitterion, ammonium, poly(oxyethylene), sugar,
    a poly(oxyethylene)-O-alkyl radical (—(CH$_2$CH$_2$O)m-Rt) where Rt is a linear, branched or cyclic alkyl, alkenyl, alkynyl radical with 6 to 20 carbon atoms,
    a COORu, CORu, COSRu, CONRvRw radical, where Ru is a poly(oxyethylene)-O-alkyl radical (—(CH$_2$CH$_2$O)m-Rt) where Rt is a linear, branched or cyclic alkyl, alkenyl, alkynyl radical with 6 to 20 carbon atoms, a glycosylalkyl radical, wherein Rv can represent a hydrogen atom or has one of the meanings given for Ru, wherein Rw has one of the meanings given for Ru, a —CONH(—C(CH$_2$ORx1)(CH$_2$ORx2)(CH$_2$ORx3)) radical, wherein Rx1, Rx2, Rx3 are such that one or two of these groups have one of the meanings given for Rm1, Rm2, Rm3 and one or two of these groups are different from a hydrogen atom and have one of the meanings given for Rd1, Rd2, Rd3, Ru, or Rx1, Rx2, Rx3 are the same or different, and are such that at least one of the groups is different from a hydrogen atom and has one of the meanings given for Ru, —Rb$_3$ is a hydrophilic group selected from:

COORe, wherein Re represents a sugar moiety, a primary, secondary or tertiary hydroxyalkyl —(CH$_2$)mOH, where m is within the range of 1 to 4, a polyoxyalkylene, in particular polyoxyethylene, having 4 to 10 alkylene oxide units, a (CH$_2$)t-NRf1Rf2 radical, where t is an integer from 1 to 5, and Rf1, Rf2, which may be the same or different, represent a hydrogen atom or a (C$_1$-C$_4$) alkyl radical, a hydroxyl group a primary, secondary or tertiary hydroxyalkyl —(CH$_2$)mOH, where m is within the range of 1 to 4, a primary, secondary, tertiary amine a quaternary ammonium N-formamide, N-alkylformamide, N-acetamide, N-alkylacetamide, N-pyrrolidonyl, CONRg1Rg2, where Rg1 and Rg2, which may be the same or different, are a hydrogen atom, a sugar moiety, a polyoxyalkylene, in particular polyoxyethylene, containing from 4 to 10 alkylene oxide units, a zwitterionic radical, a primary, secondary or tertiary hydroxyalkyl —(CH$_2$)mOH, where m is within the range of 1 to 4 (R3), COORh or CONRkRl, where Rh represents a (C$_1$-C$_5$) alkyl radical, an alkylsulfonate, or has one of the meanings given for Re or Rg1, provided that it is not a hydrogen atom, and Rk, Rl have independently one of the meanings given for Rh, and additionally one of them can represent a hydrogen atom;

x1, x2, x3 represent the percentages of the units, respectively, where x1 is between 20 and 90% x2 is between 10 and 80% x3 is between 0 and 60%, and x$_2$/x$_1$+x$_3$ is between 0.25 and 2.5; preferably between 0.25 and 2; between 0.25 and 1.5; between 0.25 and 1; or more preferably between 0.25 and 0.5; and the average molecular weight is between 500 and 100,000, advantageously between 1,000 and 50,000, between 2,000 and 25,000, more advantageously between 4,000 and 15,000, between 6,000 and 12,000, and preferably between 8,000 and 10,000, or more preferably between 9,000 and 10,000 g·mol$^{-1}$.

Advantageously, in an amphiphilic vinyl polymer of the formula (II):

Ra$_1$, Ra$_2$ and Ra$_3$ are the same or different, and represent a hydrogen atom, or a methyl radical;

Rb$_1$ represents COO$^-$M$^+$, where M$^+$ is a cationic counter-ion;

Rb$_2$ represents CONRq1Rq2, where Rq1 and Rq2 represent independently a linear or branched and/or cyclic alkyl, alkynyl or alkenyl radical containing from 3 to 50 carbon atoms, and further either one of them can represent a hydrogen atom;

Rb$_3$ represents CONRkRl, where Rk and Rl represent independently a (C$_1$-C$_5$) alkyl radical, an alkylsulfonate, a sugar moiety, a primary, secondary or tertiary hydroxyalkyl —(CH$_2$)mOH, where m is within the range of 1 to 4, a polyoxyalkylene, in particular polyoxyethylene, having 4 to 10 alkylene oxide units, a zwitterionic radical, a (CH$_2$)t-NRf1Rf2 radical, where t is an integer from 1 to 5, Rf1, Rf2 are the same or different, and represent a hydrogen atom or a (C$_1$-C$_4$) alkyl radical, and further either one of Rk and Rl can represent a hydrogen atom.

More specifically, in a particularly advantageous embodiment of a vinyl polymer of the formula (II):

Ra$_1$, Ra$_2$ and Ra$_3$ are the same or different, and represent a hydrogen atom, or a methyl radical;

Rb$_1$ represents COO$^-$M$^+$, where M$^+$ is Na$^+$ or K$^+$;

Rb$_2$ represents CONRq1Rq2, where Rq1 is n-octyl, and Rq2 is H;

x1 is between 70 and 80%, x$_2$ is between 20 and 30%, and x$_3$ is 0%; and the average molecular weight is between 2,000 and 50,000 g·mol$^{-1}$.

In another particularly advantageous embodiment of a vinyl polymer of the formula (II):

Ra$_1$, Ra$_2$ and Ra$_3$ are the same or different, and represent a hydrogen atom, or a methyl radical;

Rb$_1$ represents COO-M$^+$, where M$^+$ is a cationic counter-ion;

Rb$_2$ represents CONRq1Rq2, where Rq1 is n-octyl, and Rq2 is H;

Rb$_3$ is as defined in formula (II) above, i.e. represents CONRkRl, where Rk and Rl represent independently a (C$_1$-C$_5$) alkyl radical, an alkylsulfonate, a sugar moiety, a primary, secondary or tertiary hydroxyalkyl —(CH$_2$)mOH, where m is within the range of 1 to 4, a polyoxyalkylene, in particular polyoxyethylene, having 4 to 10 alkylene oxide units, a zwitterionic radical, a (CH$_2$)t-NRf1Rf2 radical, where t is an integer from 1 to 5, Rf1, Rf2 are the same or different, and represent a hydrogen atom or a (C$_1$-C$_4$) alkyl radical, and further either one of Rk and Rl can represent a hydrogen atom;

x$_1$ is between 30 and 40%, x$_2$ is between 20 and 30%, and x$_3$ is between 30 and 50%; and the average molecular weight is between 2,000 and 50,000 g·mol$^{-1}$.

In another embodiment, the amphiphilic molecule is an amphiphilic polymer of the amphiphilic polypeptide type, i.e. an amino acid amphiphilic polymer. In order to be amphiphilic, a polypeptide should contain a mixture of hydrophobic amino acids and hydrophilic amino acids in the above-mentioned amounts. Alternatively, a hydrophilic peptide can be modified by grafting hydrophobic side chains, and thus be provided with an amphiphilic character.

In a further embodiment, the amphiphilic molecule is an amphiphilic polymer of the amphiphilic polysaccharide type. The term <<polysaccharide>> means herein a polymer comprised of a number of monosaccharides, where a <<monosaccharide>> is a simple carbohydrate.

In a further embodiment, the amphiphilic molecule is an amphiphilic polymer of the amphiphilic dendrimer type. The term <<dendrimer>> relates to a dendritic polymer having a regular branched structure constructed by iteration processes comprising adding branched monomers having at least three reactive sites, thus providing a regular dendritic structure. Furthermore, in order to be amphiphilic, a dendrimer should be comprised of units, with some of them comprising hydrophilic groups and others hydrophobic side chains.

In an advantageous embodiment of any product according to the invention as described above, the support is a solid support. In fact, this particular embodiment is advantageous for a number of applications, in particular for providing chips carrying membrane proteins, beads coated with membrane proteins, membranes coated with membrane proteins, fibers or nanotubes coated with membrane proteins. Thus, preferably, the solid support is selected from a chip, a bead, a porous or non-porous membrane, a fiber, or a nanotube.

The term <<chip>> relates to a small plate or slide of solid material having a surface where biomolecules such as nucleic acids or proteins can be grafted.

The term <<bead>> relates to a globular, for example spherical particle. Such a bead can further have any useful characteristic for the required application, for example it can be magnetic so as to be readily separated from the media containing it.

The term <<porous membrane>> relates to a thin layer of porous and flexible material, wherein the pore size of the material lets through molecules having a size lower than a set value, and blocks molecules having a larger size.

The term <<non-porous membrane>> relates to a thin layer of flexible material, optionally shaped as bundles of thin tubes, multi-layered structures, or other devices so as to provide a several-fold increase in the surface.

The term <<fiber>> relates to a unit filament-like formation, which is generally in the form of bundles. The fibers can be <<natural>>, i.e. naturally occurring, or <<chemical>>, i.e. man-made. Examples of natural fibers include plant fibers such as cotton, linen, hemp, ramie, jute, abaca, esparto, kapok, coco, broom, henequen, kenaf, maguey, sisal, bamboo, animal fibers such as wool, alpaca, camel, Kashmir, guanaco, Angora rabbit, mohair, vicuna wool, yak, silk, and fibers of mineral origin such as asbestos. Examples of chemical fibers include artificial fibers of cellulose plant origin such as viscose, cupro, modal, of non-cellulosic origin such as alginate, fibers of animal origin such as chitin, synthetic fibers of organic origin such as polyamides, polyesters, chlorofibers, acrylics, modacrylics, polypropylene, elastodiene, elastane, polyurethane, vinylal, and synthetic fibers of mineral origin such as aramide, glass, and textile.

The term <<nanotube>> relates to a particular crystalline structure, having a hollow, tubular shape, consisting of atoms regularly distributed in the form of polygons, in particular pentagons, hexagons and/or heptagons, obtained from some materials, particularly carbon and boron nitride. Various types of nanotubes, particularly carbon nanotubes, are well-known to those skilled in the art.

In another embodiment of any product according to the invention as described above, the support is a soluble macromolecule or particle selected from polymers, dendrimers, vesicles, or micelles.

The term <<vesicle>> relates to an assembly of amphiphilic molecules consisting of one (or more) closed bilayer(s) or membrane(s) defining one (or more) aqueous internal cavity (cavities) isolated from the outside environment.

The term <<micelle>> relates to a globular, discoid or linear aggregate of molecules having a hydrophilic polar head towards the solvent side and a hydrophobic chain towards the inside.

Whatever the support, the latter should interact with the amphiphilic molecule as described above to form a bond between the support and the membrane protein complexed to the amphiphilic molecule. Various types of bonds can be formed between the support and the amphiphilic molecule.

Thus, in one embodiment of any product according to the invention as described above, the attachment of the amphiphilic molecule onto the support is mediated by a hydrophobic bond, an ionic bond, a specific receptor-ligand binding between at least one functional group in the amphiphilic molecule and at least one functional group at the support surface, or a covalent bond between at least one reactive functional group in the amphiphilic molecule and at least one reactive functional group at the support surface.

In fact, as the amphiphilic molecule has a number of hydrophobic side chains, some of these chains can interact with a support which is itself hydrophobic, irrespective of whether it is made of a hydrophobic material or coated with hydrophobic groups, such as for example alkyl groups, for example octyl groups or stearyl groups (silica, glass, quartz, or resin or other support, $C_n$-grafted, where n is between 4 and 30).

Alternatively, the binding between the support and the amphiphilic molecule can be an ionic bond between charged groups in the amphiphilic molecule and charged groups in the support. For example, in the case where the amphiphilic molecule is any vinyl polymer of the formula (II) as described above, the $CO_2^-$ groups in the vinyl polymer can form an ionic bond with positively charged groups situated on the support, either naturally or after treatment of the support or after positively charged groups have been grafted to the support (for example the quaternary ammonium group used for synthesizing anionic resins such as QAE polyoside).

An alternative way of binding the support to the amphiphilic molecule consists of a specific receptor-ligand binding between at least one group in the amphiphilic molecule and at least one molecule at the support surface, or vice versa. In fact, there are numerous molecule pairs of the receptor-ligand type, i.e. capable of specifically interacting with each other. Thus, if one or more functional groups representing the first half of a receptor-ligand molecule pair are grafted to the amphiphilic molecule, and if one or more functional groups representing the second half of the receptor-ligand molecule pair are grafted or adsorbed or attached by any means onto the support, then a specific bond can be formed between the support and the amphiphilic molecule.

Thus, in an advantageous embodiment of any product according to the invention as described above, the product is characterized in that:
a) the amphiphilic molecule further comprises at least one functional group providing the first half of a receptor-ligand molecule pair,
b) the support further comprises at least one functional group attached to the surface thereof providing the second half of said receptor-ligand molecule pair, and
c) the attachment of the amphiphilic molecule onto the support is mediated through a specific receptor-ligand binding between the functional group(s) in the amphiphilic molecule and the functional group(s) attached to the support.

As indicated above, there are numerous molecule pairs of the receptor-ligand type capable of specifically interacting with each other. For example, pairs (functional group in the amphiphilic molecule/functional group attached to the support) suitable for a product according to the invention where the interaction between the support and the amphiphilic molecule is mediated through a specific receptor-ligand binding can be selected from those pairs conventionally used in affinity chromatography, and especially from:

pairs with an interaction of the enzyme-substrate type consisting of a small molecule recognized by a protein having a high affinity for said substrate, such as the following pairs: (biotin/avidin), (glutathion/glutathion S-transferase, glutathion-binding proteins, or fusion proteins including glutathion S-transferase), (calmodulin/ATPase, protein kinase, phosphor-diesterase, or neurotransmitter), (L-arginine or p-aminobenzamidine/serine protease), (L-lysine/plasminogen (and activator)

or rRNA), (AMP, ADP, or ATP/cofactor enzyme), (lectin/glucanated protein, glucolipid, or polysaccharide), (heparin/growth and coagulation factor, steroid receptor, endonuclease, lipoprotein, or lipase), or (Cibacron Blue®/NAD or NADP cofactor enzymes, albumin, coagulation factor, or interferon), as well as the corresponding reversed pairs pairs of the (antigen/antibody) or (hapten/antibody) type, or conversely of the (antibody/antigen) or (antibody/hapten) type, pairs with an interaction of the chelation type, consisting of a group involving chelations with transition metals, such as (nitrilotriacetic acid (NTA)/transition metal), (EDTA/transition metal), pairs of the (nucleic acid/complementary nucleic acid) type, and especially (oligonucleotide/complementary oligonucleotide) type, and affinity pairs of the (phenylboronic acid (APB)/salicylhydroxamic acid (ASH)) type.

Advantageously, the pair (functional group in the amphiphilic molecule/functional group attached to the support) is selected from (biotin/avidin), (avidin/biotin), (glutathion/glutathion S-transferase), (glutathion/S-transferase glutathion), (antigen/antibody), (hapten/antibody), (antibody/antigen), (antibody/hapten), (oligonucleotide/complementary oligonucleotide).

Thus, in those products according to the present invention where the amphiphilic molecule and the support are bound through a specific receptor-ligand binding between the functional group(s) in the amphiphilic molecule and the functional group(s) attached to the support, it is particularly advantageous to use as an amphiphilic molecule a vinyl polymer of the formula (I) or (II) as generally defined above, or as provided in the advantageous embodiments of the above-described polymers of the formula (I) or (II), further comprising a percentage of between 0 and 4% of a monomer of the formula

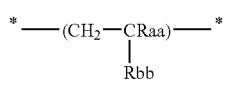
(III)

wherein:
Raa is a hydrogen atom or a methyl radical;
Rbb represents a COORcc, or —COSRcc or —CORcc or CONRccRdd group, where
  Rcc represents the functional group in the amphiphilic molecule providing the first half of the receptor-ligand pair, and
  Rdd represents a ($C_1$-$C_5$) alkyl radical, an alkylsulfonate, a hydrogen atom, a sugar moiety, a primary, secondary or tertiary hydroxyalkyl —$(CH_2)_m$OH, where m is within the range of 1 to 4, a polyoxyalkylene, in particular polyoxyethylene, having 4 to 10 alkylene oxide units, a zwitterionic radical, a $(CH_2)_t$-NRf1Rf2 radical, where t is an integer from 1 to 5, Rf1, Rf2 are the same or different, and represent a hydrogen atom or a ($C_1$-$C_4$) alkyl radical.

In these particularly advantageous products, the pair (functional group in the amphiphilic molecule/functional group attached to the support) is advantageously selected from those described above.

Lastly, it may be envisaged to attach the amphiphilic molecule on the support via a covalent bond between at least one reactive functional group in the amphiphilic molecule and at least one reactive functional group in the support (12-15). Thus, if one or more functional groups are grafted to the amphiphilic molecule and one or more functional groups which can be chemically reacted with the one or more groups in the amphiphilic molecule are adsorbed or grafted by any means on the support, it may be envisaged to chemically react together the various groups under favorable conditions suitable for forming a covalent bond between the support and the amphiphilic molecule. As regard to the reactive functional group in the amphiphilic molecule and the reactive functional group in the support capable of forming a covalent bond under favorable conditions, they will thus be referred to as a <<chemical reactive pair>>.

Thus, in an advantageous embodiment of any product according to the invention as described above, the product is characterized in that:
  a) the amphiphilic molecule further comprises at least one functional group providing the first half of a chemical reactive pair,
  b) the support further comprises at least one functional group attached to the surface thereof providing the second half of said chemical reactive pair, and
  c) the attachment of the amphiphilic molecule to the support is carried out by chemically reacting the functional group(s) in the amphiphilic molecule with the functional group(s) attached to the support.

As an example, it would be possible to envisage the use of a process known for having a high selectivity which comprises adsorbing at the surface a quinone derivative which, under certain conditions compatible with our experiments, will react spontaneously through a Diels-Alder mechanism with a cyclopentadienyl group attached to the amphiphilic molecule. The resulting bonds are covalent.

Also, it is possible to envisage the same type of selective reaction between a support having azide groups ($N_3$) on the surface thereof and an amphiphilic polymer having an alkynyl group (triple bond).

Also, it may be envisaged to functionalize the amphiphilic molecule with an alkoxylamine group (or a carbonyl group) capable of condensing with a high selectivity on a carbonyl function (or an alkoxylamine group) attached to the support surface. The resulting bond (alkoxylimine) is covalent.

Thus, in the products according to the present invention where the amphiphilic molecule and the support are covalently bound through the reactive functional group(s) in the amphiphilic molecule and the reactive functional group(s) attached to the support, it is particularly advantageous to use as an amphiphilic molecule a vinyl polymer of the formula (I) or (II) as generally defined above, or as provided in the advantageous embodiments of the above-described polymers of the formula (I) or (II), further comprising a percentage of between 0 and 4% of a monomer of the formula:

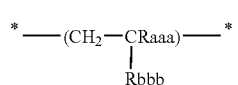
(IV)

wherein:
Raaa is a hydrogen atom or a methyl radical;
Rbbb represents a COORccc, or —COSRccc or —CORccc or CONRcccRddd group, where
  Rccc represents the reactive functional group in the amphiphilic molecule providing the first half of a chemical reactive pair, and Rdd represents a ($C_1$-$C_5$) alkyl radical, an alkylsulfonate, a hydrogen atom, a sugar moiety, a primary, secondary or tertiary hydroxyalkyl —($CH_2$)mOH, where m is within the range of 1 to 4, a polyoxyalkylene, in particular polyoxyethylene, having 4 to 10 alkylene oxide units, a zwitterionic radical, a ($CH_2$)t-NRf1Rf2 radical, where t is an integer from 1 to 5, Rf1, Rf2 are the same or different, and represent a hydrogen atom or a ($C_1$-$C_4$) alkyl radical.

In these particularly advantageous products, the pair (reactive functional group in the amphiphilic molecule/reactive functional group attached to the support) is advantageously selected from those described above.

The products according to the invention described above can have, attached to their surface through the amphiphilic molecule, any membrane protein. One of the great advantages provided according to the invention, is that any membrane protein, irrespective of its structure, its function, and whether it is known or not, can be immobilized on a support in the form of a product according to the invention. In some embodiments, the one or more membrane protein(s) immobilized at the support surface is (are) selected from an antigen, an antibody, an enzyme, a cell receptor, an ion channel, or a membrane protein of viral, bacterial, or eukaryotic origin. The one or more membrane protein(s) immobilized at the support surface can be selected depending on the required end use of the product according to the invention.

The invention also relates to a process for preparing a product according to the invention as described above, comprising:
a) providing at least one membrane protein, a support and an amphiphilic molecule as described above in any embodiment,
b) forming a complex between the amphiphilic molecule and the membrane protein, and
c) attaching the amphiphilic molecule of the complex to the support via a hydrophobic bond, an ionic bond, a specific receptor-ligand binding between at least one functional group in the amphiphilic molecule and at least one functional group at the support surface, or a covalent bond between at least one reactive functional group in the amphiphilic molecule and at least one reactive functional group at the support surface.

As an example, forming the complex between the amphiphilic molecule and the membrane protein (step b) can be carried out as follows (7-10):
to a solution of membrane protein(s) made soluble by means of a detergent at a concentration higher than its critical micelle concentration, a weight amount of amphiphilic molecule of 0.5 to 10 times the weight of protein is added.
After incubating 15 min at 4° C., the detergent is removed either by adsorption on Bio-Beads®, or by dialysis, or by diluting to a level lower than the detergent critical micelle concentration followed by concentrating the preparation on a filtration system which lets the detergent through but not the protein (Centricon® or Amicon® system, for example), or by precipitating the detergent, and the like. Several of these procedures can also be used sequentially to allow for complete removal of the detergent.
At this stage and depending on the nature and size of the protein used, the complexes can then be washed to remove the excess amphiphilic molecule either by centrifuging the preparation on a gradient of sucrose, or by separating the complexes from the amphiphilic molecules on molecular sieves or affinity column.

Alternatively, forming membrane protein(s)/amphiphilic molecule complexes can be carried out by various other routes such as direct extraction, optionally assisted by the presence of a detergent, of proteins from the starting preparations (biological membranes, inclusion bodies and the like), trapping during a renaturation process, cell-free synthesis and the like.

There are various ways of attaching the amphiphilic molecule of the complex to the support (step c): thus, as an example, in the case of solid supports, solutions of the membrane protein(s)-amphiphilic molecule complex can be deposited on the support, providing that optimal conditions are used for forming the interaction between the amphiphilic molecule and the support (for example, for avidin/biotin interaction, in a NaCl, pH=7.4 buffer): the incubation time will depend both on the nature of the support, and on the type of amphiphilic molecule/support interaction selected.

The products according to the invention, obtained by the processes described above, have a number of possible applications, in particular in terms of diagnosis, drug design, or biotechnologies.

Thus, the invention relates in particular to the use of a product according to the invention comprising a support and at least one membrane protein attached to the surface thereof as described above for detecting the presence or absence in a biological specimen of a ligand of said at least one membrane protein.

The term <<biological sample>> relates to any type of sample containing biological matter. In particular, such a biological specimen can be selected from a blood sample, a lymph sample, a serum sample, a urine sample, a stool sample, a saliva sample, a tissue sample, or a biopsy. The sample can derive from any type of organism, in particular from a human being, an animal, a microorganism, a virus or a plant. The raw sample, collected from the organism of interest, can subsequently be processed to make it acceptable for the subsequent assay method. This will not be the case when the molecule to be detected is directly available in the sample. On the contrary, if the molecule to be detected is not directly available in the sample, the sample will have to be processed to make it available. For example, if the sample contains cells that are not in solution and the ligand to be detected is itself membrane-like, the sample can be processed to provide a solution of cells having on their surface the directly detectable ligand. If the ligand to be detected is an intracellular molecule, the sample should be processed so that the ligand is directly available. For example if the ligand to be detected is an intracellular protein, there are a number of techniques well-known to those skilled in the art for extracting proteins from a biological specimen. If the ligand to be detected is a nucleic acid, there are also a number of techniques well-known to those skilled in the art for extracting nucleic acids from a biological specimen. The same is true for other types of ligands like lipids or sugars.

Detecting the presence or absence of the membrane protein ligand in the biological specimen can be carried out by different techniques known to those skilled in the art. For example, detecting ligand binding to the membrane protein can be carried out using the surface plasmon resonance technique, which allows detection and real-time monitoring of interactions between circulating molecules and one or more immobilized molecule(s), by continuously observing for a change in surface plasmon resonance induced by the interaction of the circulating molecules with the chip as an assay support. But ligand binding to the immobilized membrane protein can also be detected by other techniques. In particular, if the ligand tested for its presence is known, it is possible to use well-known ELISA-type techniques, where the ligand attached to the membrane protein is detected by means of a third molecule specifically binding to this ligand (for example a specific antibody, or if the ligand can bind several membrane proteins simultaneously, a second membrane protein in a soluble form), this third molecule being detectable by fluorescence emission, enzyme reaction, its radioactivity, or any other means conventionally used for this type of technique.

More specifically, such a use of a product according to the invention for detecting the presence or absence in a biological specimen of a ligand of said at least one membrane protein can be applied for diagnosing the presence or absence of a membrane protein ligand in a biological specimen. In particular, in the case where said at least one membrane protein is a membrane antigen of a pathogenic agent, a product according to the invention comprising a support and said membrane antigen of a pathogenic agent attached to the surface thereof as described above can be used for diagnosing in a subject the presence or absence of an exposition to this pathogenic agent, by detecting the presence or absence of antibodies raised against said antigen in the serum of the subject. Thus, in an advantageous embodiment of such a use, said at least one membrane protein is a membrane antigen of a pathogenic agent, said biological specimen is a serum sample, and said ligand to be detected is an antibody raised against said antigen.

The invention also relates to the use of a product according to the invention comprising a support and at least one membrane protein attached to the surface thereof as described above for screening a compound bank for ligands of said at least one membrane protein.

In fact, such a use is very useful in pharmacology for membrane proteins providing therapeutic targets. For each new membrane target identified, a screening of compound libraries is generally carried out to identify various agonist or antagonist, potential drug candidate ligands, for the target in question, these candidates then being optimized in terms of efficiency and non-toxicity.

As indicated above, the advantage of the products according to the invention for such an application is that the membrane proteins immobilized on the support, as they are complexed with the amphiphilic molecule, are fully soluble in an aqueous solution, and biochemically stabilized in their natural conformation. Thus, detection can be carried out in an aqueous medium while keeping the native structure of the membrane protein, thus allowing not only to simplify the binding detection method, but also to make sure that the test membrane protein is definitely in its native state, and accordingly likely to bind, with the same affinity, the same compounds as within the living organism.

In this case, besides the above-described techniques for detecting a ligand binding to the membrane protein, it is possible to use test compounds which are directly detectable by fluorescence, colorimetry or any other type of detection.

The invention further relates to the use of a product according to the invention comprising a support and at least one membrane protein attached to the surface thereof as described above, wherein said at least one protein is an enzyme, for transforming said enzyme substrate under controlled conditions. In fact, a product according to the invention can be in particular a functionalized membrane, i.e. a membrane on which a <<lawn>> of membrane enzyme is immobilized, this more or less regular enzyme distribution on the membrane having been brought about by means of a process according to the invention. In fact, this allows in particular to convert a solution of one of this membrane enzyme substrate to a solution of the product generated after action of the enzyme on this substrate by simply filtrating the solution through the thus functionalized membrane, or sending the solution through a bundle of tubes having an internal surface to which the membrane enzyme is attached according to the invention.

The invention generally relies on the principle involving using amphiphilic molecules for immobilizing any membrane proteins on a support, in the absence of a detergent or at detergent concentrations lower than the critical micelle concentration (CMC), and under such conditions that the membrane protein is biochemically stabilized.

Accordingly the invention also relates to a kit for carrying out a process for preparing a product according to the invention as described above, comprising a support and an amphiphilic molecule, characterized in that said amphiphilic molecule and said support interact through a hydrophobic bond, an ionic bond, a specific receptor-ligand binding between at least one functional group in the amphiphilic molecule and at least one functional group at the support surface, or a covalent bond between at least one reactive functional group in the amphiphilic molecule and at least one reactive functional group at the support surface. The support and the amphiphilic molecule can be any type of support or amphiphilic molecule as described above, provided that both parts of the kit, i.e. the support and the amphiphilic molecule, interact through a hydrophobic bond, an ionic bond, a specific receptor-ligand binding between at least one functional group in the amphiphilic molecule and at least one functional group at the support surface, or a covalent bond between at least one reactive functional group in the amphiphilic molecule and at least one reactive functional group at the support surface.

In an advantageous embodiment of such a kit according to the invention, the support and the amphiphilic molecule interact through a specific receptor-ligand binding between at least one functional group in the amphiphilic molecule and at least one functional group at the support surface. More specifically, preferably the kit is characterized in that:
a) the amphiphilic molecule further comprises at least one functional group providing the first half of a receptor-ligand molecule pair,
b) the support further comprises at least one functional group attached to the surface thereof providing the second half of said receptor-ligand molecule pair, and
c) the binding of the amphiphilic molecule to the support is mediated through a specific receptor-ligand binding between the functional group(s) in the amphiphilic molecule and the functional group(s) attached to the support.

Advantageously, the pair (functional group in the amphiphilic molecule/functional group attached to the support) is selected from the following pairs: (biotin/avidin), (glutathion/glutathion S-transferase, glutathion-binding proteins, or fusion proteins including glutathion S-transferase), (calmoduline/ATPase, protein kinase, phosphodiesterase, or neurotransmitter), (L-arginine or p-aminobenzamidine/serine protease), (L-lysine/plasminogen (and activator) or rRNA), (AMP, ADP, or ATP/cofactor enzyme), (lectin/glucanated protein, glucolipid, or polysaccharide), (heparin/growth and coagulation factor, steroid receptor, endonuclease, lipoprotein, or lipase), or (Cibacron Blue®/NAD or NADP cofactor enzymes, albumin, coagulation factor, or interferon), or the corresponding reversed pairs, (antigen/antibody), (hapten/antibody), (antibody/antigen), (antibody/hapten), (nitrilotriacetic acid (NTA)/transition metal), (EDTA/transition metal), (phenylboronic acid (APB)/salicylhydroxamic acid (ASH)), or (oligonucleotide/complementary oligonucleotide).

In a kit according to the present invention where the amphiphilic molecule and the support are bound through a specific receptor-ligand binding between the functional group(s) in the amphiphilic molecule and the functional group(s) attached to the support, it is particularly advantageous to use as an amphiphilic molecule a vinyl polymer of the formula (I) or (II) as generally defined above, or as provided in the advantageous embodiments of the above-described polymers of the formula (I) or (II), further comprising a percentage of between 0 and 4% of a monomer of the formula:

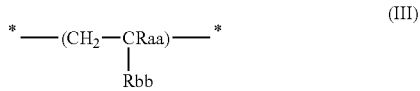

wherein:

Raa is a hydrogen atom or a methyl radical;

Rbb represents a COORcc, or —COSRcc or —CORcc or CONRccRdd group, where

Rcc represents the functional group in the amphiphilic molecule providing the first half of the receptor-ligand pair, and Rdd represents a ($C_1$-$C_5$) alkyl radical, an alkylsulfonate, a hydrogen atom, a sugar moiety, a primary, secondary or tertiary hydroxyalkyl —($CH_2$)mOH, where m is within the range of 1 to 4, a polyoxyalkylene, in particular polyoxyethylene, having 4 to 10 alkylene oxide units, a zwitterionic radical, a ($CH_2$)t-NRf1Rf2 radical, where t is an integer from 1 to 5, Rf1, Rf2 are the same or different, and represent a hydrogen atom or a ($C_1$-$C_4$) alkyl radical.

In this case, the pair (functional group in the amphiphilic molecule/functional group attached to the support) is advantageously selected from those described above.

In another preferred embodiment of a kit according to the invention, the support and the amphiphilic molecule interact via a covalent bond between at least one reactive functional group in the amphiphilic molecule and at least one reactive functional group in the support. More specifically, preferably, the kit is characterized in that:

a) the amphiphilic molecule further comprises at least one functional group providing the first half of a chemical reactive pair, b) the support further comprises at least one functional group attached to the surface thereof providing the second half of said chemical reactive pair, and c) the binding of the amphiphilic molecule to the support is carried out by chemically reacting the functional group(s) in the amphiphilic molecule with the functional group(s) attached to the support.

In a kit according to the present invention where the amphiphilic molecule and the support are covalently bound between the reactive functional group(s) in the amphiphilic molecule and the reactive functional group(s) attached to the support, it is particularly advantageous to use as an amphiphilic molecule a vinyl polymer of the formula (I) or (II) as generally defined above, or as provided in the advantageous embodiments of the above-described polymers of the formula (I) or (II), further comprising a percentage of between 0 and 4% of a monomer of the formula:

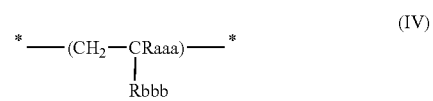

wherein:

Raaa is a hydrogen atom or a methyl radical;

Rbbb represents a COORccc, or —COSRccc or —CORccc or CONRcccRddd group, where

Rccc represents the reactive functional group in the amphiphilic molecule providing the first half of a chemical reactive pair, and Rdd represents a ($C_1$-$C_5$) alkyl radical, an alkylsulfonate, a hydrogen atom, a sugar moiety, a primary, secondary or tertiary hydroxyalkyl —($CH_2$)mOH, where m is within the range of 1 to 4, a polyoxyalkylene, in particular polyoxyethylene, having 4 to 10 alkylene oxide units, a zwitterionic radical, a ($CH_2$)t-NRf1Rf2 radical, where t is an integer from 1 to 5, Rf1, Rf2 are the same or different, and represent a hydrogen atom or a ($C_1$-$C_4$) alkyl radical.

In these kits, the pair (reactive functional group in the amphiphilic molecule/reactive functional group attached to the support) is advantageously selected from those described above.

The invention further relates to the use of an amphiphilic molecule for complexing a membrane protein and attaching it to a support. Said amphiphilic molecule, said membrane protein and said support can be any one from the group consisting of amphiphilic molecules, membrane proteins and supports, as described above.

Lastly, the invention also relates to any amphiphilic molecule as defined above, further comprising at least one functional group providing the first half of a receptor-ligand molecule pair or the first half of a chemical reactive pair.

In a first embodiment, the amphiphilic molecule further comprises at least one functional group providing the first half of a receptor-ligand molecule pair. Such a functionalized amphiphilic molecule allows binding any membrane protein to a support comprising at least one functional group attached by any means to the surface thereof providing the second half of said receptor-ligand molecule pair through a specific receptor-ligand binding between the functional group(s) in the amphiphilic molecule and the functional group(s) attached to the support. Advantageously, the functional group(s) in the amphiphilic molecule are selected from biotin, avidin, glutathion, glutathion S-transferase, calmoduline, an ATPase, a protein kinase, a phosphodiesterase, a neurotransmitter, L-arginine, p-aminobenzamidine, a serine protease, L-lysine, plasminogen (and activator), an rRNA, AMP, ADP, ATP, a cofactor enzyme, a lectin, a glucanated protein, a glucolipid, a polysaccharide, heparin, a growth and coagulation factor, a steroid receptor, an endonuclease, a lipoprotein, a lipase, Cibacron Blue®, a NAD or NADP cofactor enzyme, albumin, a coagulation factor, an interferon, an antigen, a hapten, an antibody, nitrilotriacetic acid (NTA), EDTA, phenylboronic acid (APB), salicylhydroxamic acid (ASH), an oligonucleotide, a cyclopentadienyl group, an alkynyl group or an alkoxylamine group. Preferably, the functional group(s) in the amphiphilic molecule are selected from biotin, avidin, glutathion, glutathion S-transferase, an antigen, a hapten, an antibody, nitrilotriacetic acid (NTA), EDTA or an oligonucleotide.

Furthermore, the amphiphilic molecule is advantageously a polymer of the formula (I) or (II) further comprising a percentage of between 0 and 4% of a monomer of the formula

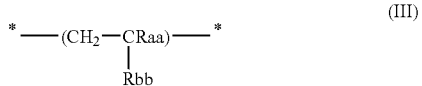

in which Raa and Rbb are as defined above.

In a second embodiment, the amphiphilic molecule further comprises at least one functional group providing the first half of a chemical reactive pair. Such a functionalized amphiphilic molecule allows binding any membrane protein to a support comprising at least one reactive functional group attached by any means to the surface thereof providing the second half of said chemical reactive pair through a covalent bond between the reactive functional group(s) in the amphiphilic molecule and the reactive functional group(s) attached to the support. Advantageously, the reactive functional group(s) in the amphiphilic molecule are selected from those described above.

Furthermore, the amphiphilic molecule is advantageously a polymer of the formula (I) or (II) further comprising a percentage of between 0 and 4% of a monomer of the formula

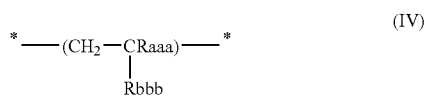

wherein Raaa and Rbbb are as defined above.

Another application of the products according to the invention comprising a support and at least one membrane protein attached to the surface thereof using an amphiphilic molecule with which said membrane protein is complexed as described above involves using such a product as a transient step in a process for assaying membrane proteins in a sample by mass spectrometry.

In fact, mass spectrometry, a very valuable technique in proteomics for identifying proteins, is made a lot more difficult, in the case of membrane proteins, due to the presence of detergents, which interfere with the detection of the proteins or peptides derived therefrom upon mild proteolysis. Immobilization through amphiphilic molecules as described above provides a very smart means to overcome this problem by removing the detergents while still allowing partial proteolysis of the membrane proteins immobilized on a support using an amphiphilic molecule (see FIG. 8).

Accordingly the present invention also relates to a process for assaying membrane proteins in a sample, comprising the preparation of a product according to the invention comprising a support and at least one membrane protein attached to the surface thereof through an amphiphilic molecule with which said membrane protein is complexed as described above.

In a preferred embodiment, the process comprises the steps of:
a) solubilizing membrane proteins in a detergent,
b) complexing the membrane proteins with an amphiphilic molecule as described above and removing the detergent,
c) immobilizing the membrane proteins on a support as described above through the amphiphilic molecule,
d) extensively washing and adding a protease for generating protein fragments of membrane proteins, with the transmembrane domain remaining complexed with the amphiphilic molecule attached to the support,
e) removing the support to which the transmembrane domain complexed with the amphiphilic molecule remains bound and analyzing the protein fragments by mass spectrometry.

The various supports, amphiphilic molecules and types of bonds between the amphiphilic molecule and the support described above can be used in this application of the invention.

In an advantageous example, the support can particularly consist of magnetic beads, which can be readily separated at step e) by means of a magnet.

An advantageous amphiphilic molecule can be in particular any vinyl polymer as described above.

The amphiphilic molecule can be for example biotinylated and the support coated with avidin for binding the amphiphilic molecule to the support.

These various preferred embodiments may of course be combined.

EXAMPLES

Example 1

Membrane Protein Immobilization at the Surface of Streptavidin-Carrying Chips by Means of a Biotinylated Amphipol 1.1 Principle The experimental principle developed for immobilizing membrane proteins at the surface of solid supports is the following (FIG. 2): the membrane protein is solubilized in a detergent (step a) then trapped with a biotinylated amphipol and the detergent is removed (step b); the resulting complex is contacted with a support grafted with streptavidin groups with which it can be combined via a specific biotin/streptavidin interaction (step c). A protein ligand can then be circulated on the support and the ligand/protein interaction can be studied (step d).

Immobilization was experimentally monitored by a surface plasmon resonance (SPR) technique. This technique allows detection and real-time monitoring of interactions between circulating molecules and one or more immobilized molecule(s), by continuously observing for a change in surface plasmon resonance induced by the circulating molecules interacting with the assay support. The result of an SPR experiment enables to monitor the amount of materiel interacting with the support with time.

1.2 Synthesis of Biotinylated Amphipol (BApol) and Behavior in a Solution 1.2.1 Synthesis of Biotinylated Amphipol (BApol)

Figure 3:
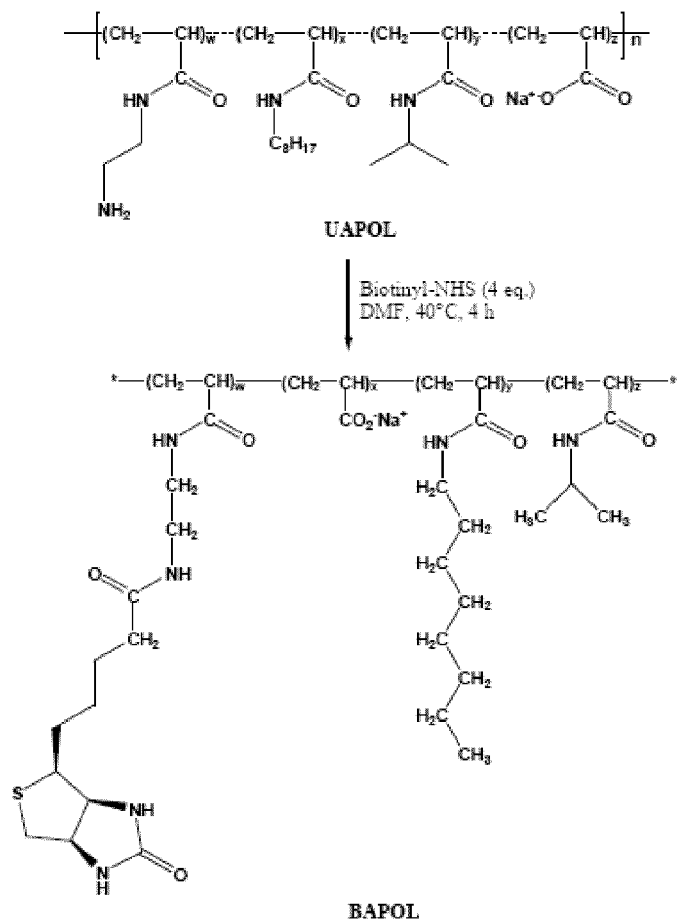
FIG. 3. Chemical structures of universal amphipol (UAPol) and biotinylated amphipol (BAPol). Detail of the biotinylation reaction.

The BAPol structure is described in FIG. 3.

Figure 1:
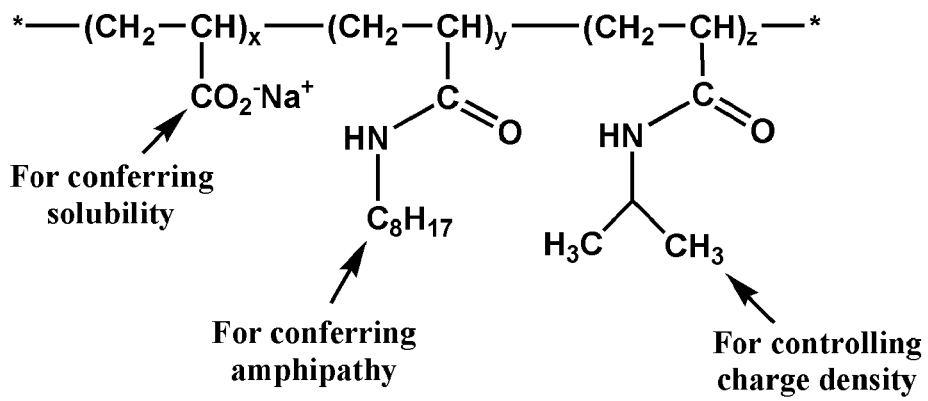
FIG. 1. Amphipols and membrane protein/amphipol complexes. A, chemical structure of an amphipol (APol). A molecule of amphipol A8-35 has an average molecular weight of about 10 kDa. It contains about 18 octyl chains, which endow it with hydrophobicity and a very high affinity for the protein surface. B, modelization of the complex formed by combining amphipols with cytochrome $bc_1$, a membrane protein complex of 500 kDa. The amphipol belt bound to the protein contains about 8 A8-35 molecules (8).
Figure 1:
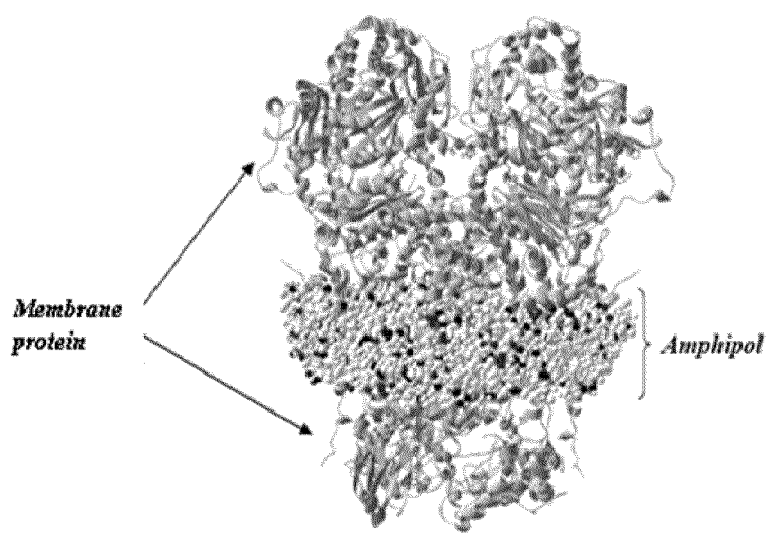
Figure 2:
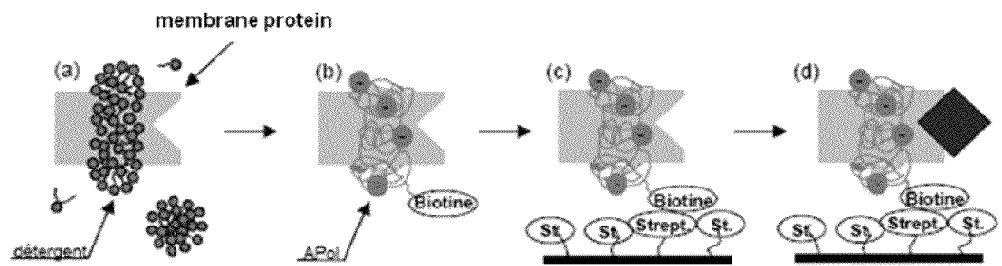
FIG. 2. Principle of the method developed. Step a. The protein (light grey rectangle) is solubilized with a detergent. Step b. The protein is trapped with a biotinylated amphipol (BAPol), and the detergent is removed. Step c. The protein/BAPol complex interacts via biotin/avidin coupling with a solid support grafted with avidin. Step d. A ligand (dark grey diamond) recognizes the target protein.

The method for synthesizing BAPol is derived from the method for synthesizing non-functionalized amphipols (7, 16-17). It comprises forming amide bonds with carboxylic acid functionalities of a low molecular weight polyacrylic acid and appropriately selected alkylamines, such as isopropylamine and octylamine, as well as, in this particular case, a low proportion of selectively monoprotected ethylenediamine. Upon deprotection of the amine functionality not bound to the polymer, a functionalized amphipol ("universal" amphipol, or "UAPol"; FIG. 2) is obtained, which can then be reacted on any sufficiently active substrate. Thus, BAPol is obtained by reaction of the UAPol amine functionality with D-biotin succinimidyl ester (FIG. 3).

1.2.2 Assay

The BAPols' characteristics in solution are the same as non-biotinylated APols. In particular, they form particles having the same size and molecular weight distribution.

Furthermore, the membrane proteins trapped with BAPols are properly maintained in solution (they do not aggregate in the absence of a detergent), the same as with non-biotinylated amphipols.

In summary, although a biotin molecule has been grafted, the BAPols have the same physicochemical and biochemical characteristics as biotin-free APols, except for their capacity to bind specifically to avidin or streptavidin. It is therefore possible to use them for complexing membrane proteins and making them water-soluble in the absence of a detergent, and then to combine them with a support.

1.3 Amphipol Interaction with a Support Grafted with Streptavidin Groups

Solutions of non-biotinylated amphipol (HAPol) and biotinylated amphipol (BAPol) were injected separately on two separate channels of a support grafted with streptavidin groups (SA support).

Figure 4:
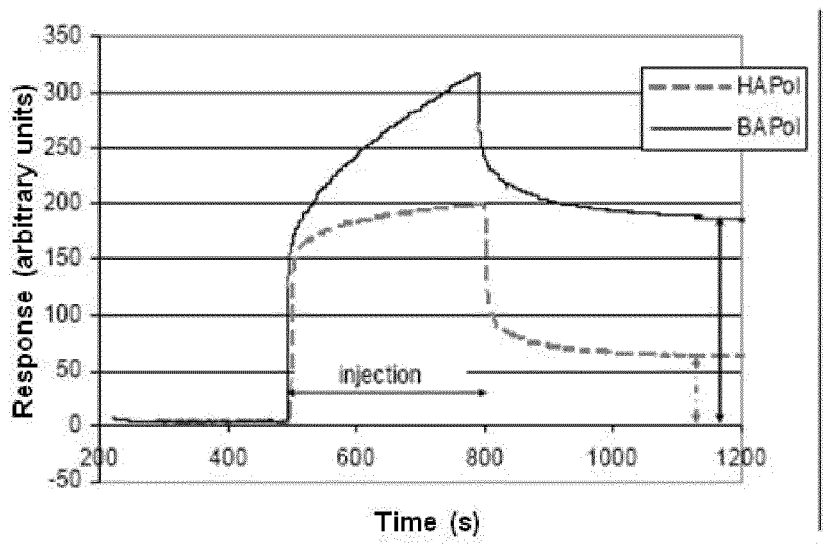
FIG. 4. Comparison between the adsorption of a biotinylated amphipol (BAPol) and another non-biotinylated amphipol (HApol) onto an avidin-carrying chip, followed by surface plasmon resonance (SPR). Recordings resulting from injections on two separate channels of 50 µl HAPol (in dotted grey) or BAPol (in black) diluted to 10 µM in a NaCl-HEPES buffer (150 mM NaCl, 10 mM HEPES, pH=7.4). The same buffer is flown continuously on the chip outside the injection periods, at 10 µl/min. The difference in amplitude of the plateaus observed after injection, represented by vertical arrows, shows that polymer adhesion to the chip is mediated by biotin.

The results obtained show that both polymers adhere to the SA support after injection (FIG. 4), but that the weight of bound BAPol is about three times that of HAPol.

Since only biotin grafting distinguishes both polymers, this experiment confirms that high adsorption of amphipol on the chip results from the presence of biotin.

1.4 Deposition of Membrane Proteins Trapped in BAPol and Test for Ligand Recognition The four following model membrane proteins having a well-known biochemistry and the APol behavior of which had already been tested were used to test the process for immobilizing membrane proteins according to the invention: the transmembrane domain of the OmpA protein (tOmpA), bacteriorhodopsin (BR), $b_6f$ cytochrome ($b_6f$) and $bc_1$ cytochrome ($bc_1$).

Furthermore, rabbit sera containing antibodies raised against each of these four proteins were prepared as ligands for monitoring membrane proteins/ligands interactions by SPR.

1.4.1 Method for Binding Membrane Proteins on SA Support

The four proteins were trapped in BAPol:

tOmpA is available in solution at a concentration of 1.2 g/l in the presence of octyltetraoxyethylene detergent ($C_8E_4$) to 6 g/l. Trapping is carried out by adding 18 µl of a 100 g/l BAPol solution in water to 500 µl of protein solution (i.e. 4 g of BAPol per g of tOmpA). After incubation for 15 min, 30 mg of Bio-beads are added and incubation is left to proceed under stirring for 3 hr at 4° C. followed by recovery of the solution and removal of the Bio-beads.

The BR solution in octyl thioglucoside detergent (OTG) contains 1 g/l protein, 20 mM of OTG. 23 µl of a 100 g/l BAPol solution in water are added to 450 µl of protein solution (i.e. 5 g of BAPol per g of BR). After incubation for 15 min, 30 mg of Bio-beads are added and incubation is left to proceed under stirring for 3 hr at 4° C. followed by recovery of the solution and removal of the Bio-beads.

The $b_6f$ solution in lauryl maltoside detergent (LM) contains 0.27 g/l protein and 0.1 g/l LM. 1.2 µl of a 100 g/l BAPol solution in water is added to 150 µl of protein solution (i.e. 3 g of BAPol per g of $b_6f$). After incubation for 15 min, 140 mg of Bio-beads are added and incubation is left to proceed under stirring for 3 hr at 4° C. followed by recovery of the solution and removal of the Bio-beads.

The $bc_1$ solution in LM contains 35 g/l protein and 0.1 g/l of LM. 119 µl of a 100 g/l BAPol solution in water are added to 225 µl of protein solution (i.e. 1.5 g of BAPol per g of $bc_1$). After incubation for 15 min, 90 mg of Bio-beads are added and incubation is left to proceed under stirring for 3 hr at 4° C. followed by recovery of the solution and removal of the Bio-beads.

Then, the resulting proteins/BAPol complexes and the BAPol alone were deposited on separate channels of an SA support: all solutions are adjusted to a concentration of 30 µM of BAPol by diluting with NaCl-HEPES buffer (150 mM NaCl, 10 mM HEPES at pH 7.4), and are then injected in an amount of 100 µl each on a Biacore 2000 instrument so that each solution passes through separate channels on SA supports. In the intervals between injections, NaCl-HEPES buffer is circulated. The circulation flow is set at 10 µl/min during and between injections.

Figure 5:
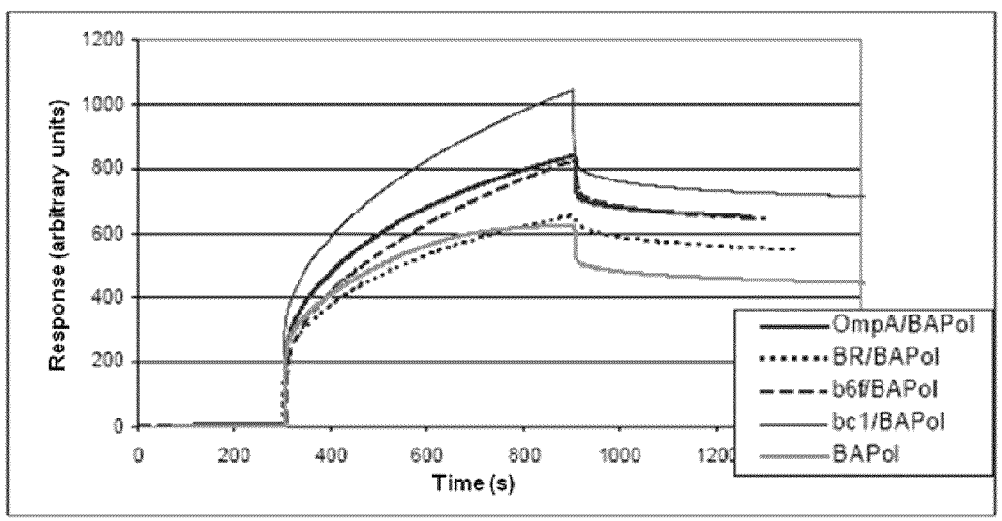
FIG. 5. Adhesion of membrane protein/amphipol complexes onto an avidin-carrying chip followed by SPR. Recordings resulting from injection of 100 µl solutions of BAPol, tOmpA/BAPol, BR/BAPol, $b_6f$/BAPol and $bc_1$/BAPol at constant BAPol concentration of 30 µM on different channels of an avidin-carrying chip. Circulating buffer: NaCl-HEPES.

The experiment shows that the material becomes effectively and irreversibly bound to the supports (FIG. 5).

1.4.2 Ligand Binding Assay to Membrane Proteins Immobilized on SA Support by BApol Antibody/immobilized material recognition experiments were subsequently carried out with purified sera only keeping any antibodies, diluted 100× in NaCl-HEPES buffer.

In brief, 10 µl of pre-immune purified sera (pre-i.) are injected followed by post-immune sera raised against tOmpA (Post-i.-OA), against BR (Post-i.-BR), against $b_6f$ (Post-i.-b6f), and then against bc1 (Post-i.-bc1) onto channels previously coated with BAPol or proteins trapped in BAPol. The injection period is 60 s and time zero is shown by an arrow. Between injections, the NaCl-HEPES buffer (NaCl 150 mM, HEPES 10 mM pH=7.4) is flown on the support. Each recording is obtained on a channel coated with a different sample.

Figure 6:
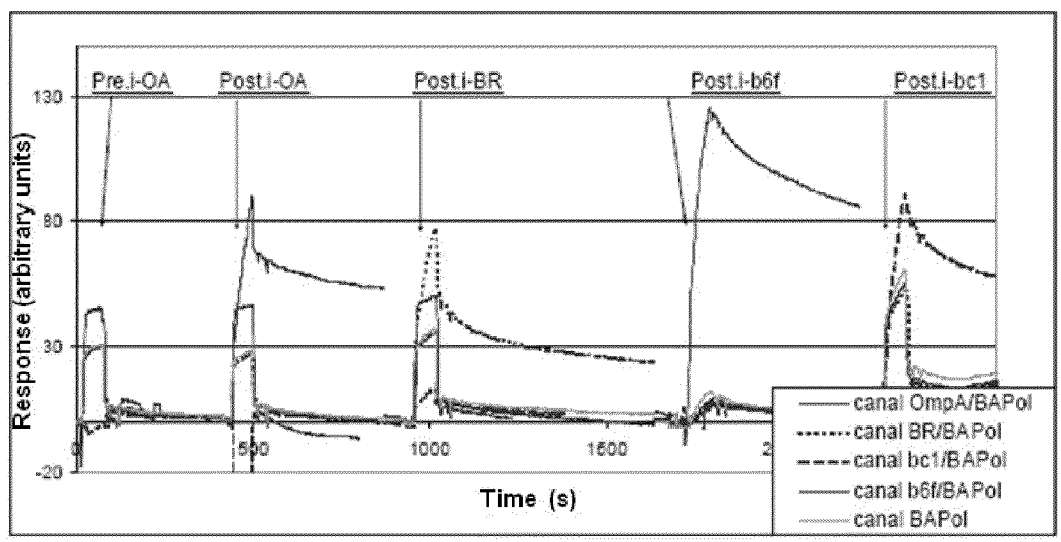
FIG. 6. Detection by surface plasmon resonance (SPR) of antibody binding to membrane proteins immobilized at the surface of an avidin-carrying chip through a biotinylated amphipol. 10 µl of pre-immune (pre-i.), then post-immune purified sera raised against tOmpA (Post-i.-OA), against BR (Post-i.-BR), against $b_6f$ (Post-i.-b6f), or against bc1 (Post-i.-bc1), are injected sequentially on channels previously coated with BAPol or proteins trapped in BAPol. The injections are indicated by arrows. Each recording is performed on a channel coated with a different sample: the thick black line recording refers to the channel where tOmpA/BAPol complexes are immobilized, the small dotted thin black line refers to the BR/BAPol channel, the large dotted thin black line refers to the $b_6f$/BAPol channel, the thin black line refers to the $bc_1$/BAPol channel, and the thick grey line refers to the channel for the BAPol only, control sample. Circulating buffer: NaCl-HEPES.

All responses observed are specific (see FIG. 6): on the whole, the results show that the SPR signal remains high after injection only when the post-immune sera are tested and providing that they flow on the channel carrying the protein used for immunization (against which serum antibodies were produced).

This confirms that membrane proteins were immobilized on the channels supports. This also shows that the process developed may conveniently be used for monitoring interactions between membrane proteins and ligands.

Furthermore, the same experiment was carried out with non-purified sera and lead to the same conclusion, thus showing that a specific ligand can be detected even inside an extremely complex media like a non-purified serum (results not shown).

1.5 Determination of the Protein Immobilization Mediating Agent on the Support.

In a control experiment, the response obtained either when the test protein was deposited on the chip after trapping in HAPol (non-biotinylated) or after trapping in BAPol (biotinylated) was compared, in order to check whether protein binding to SA support is mediated by the biotin covalently bonded to the polymer, via specific biotin/streptavidin binding.

Figure 7:
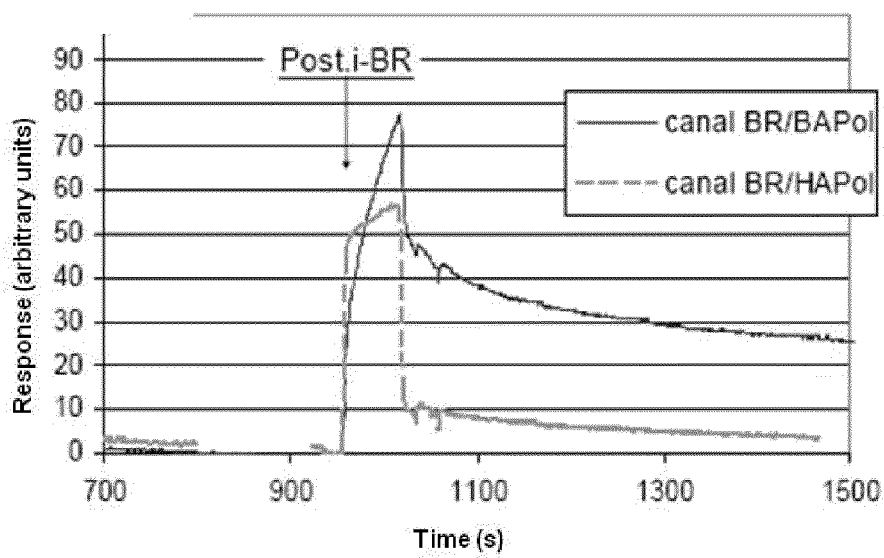
FIG. 7. Detection by SPR of antibody binding on a protein bound to the surface of an avidin-carrying chip after trapping in HAPol or BAPol. Recordings obtained upon injection of post-immune serum raised against BR on channels coated with BR after trapping either with HAPol (in dotted grey), or with BAPol (in black). Circulating buffer: NaCl-HEPES. The experiment shows an increase in the signal when adsorption is mediated by a functionalized amphipol.
Figure 8:
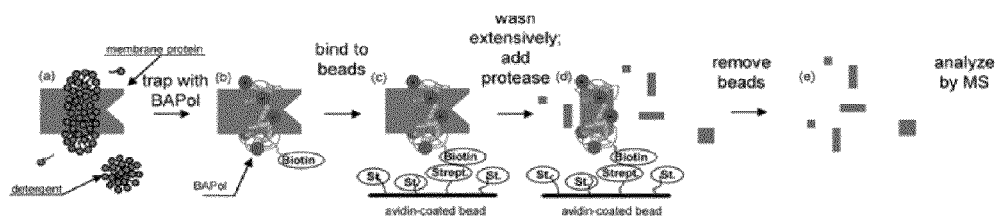
FIG. 8. Use of a product according to the invention for analyzing membrane proteins by mass spectrometry. Step (a). The protein (light grey rectangle) is solubilized into a detergent. Step (b). The protein is trapped (or complexed) with a biotinylated amphipol (BAPol), and the detergent is removed. Step (c). The complex membrane protein/BAPol interacts via biotin/avidin coupling with a solid support grafted with avidin. Step (d). After extensive washing, a protease is added to carry out a mild proteolysis and generate membrane protein fragments, with the transmembrane portion still being protected by the amphipol with which it is complexed. Step (e). After separation from the support which still carries fragments of transmembrane portions complexed with biotinylated amphipol BAPol (for example by means of a magnet in case of magnetic beads), the remaining, soluble fragments are analyzed by mass spectrometry.

The results (see FIG. 7) show that the antibody only significantly binds, and therefore only recognizes the protein deposited on SA support, if the latter was trapped in BAPol.

1.6 Conclusion.

These results demonstrate the reliability and potency of the process according to the invention for immobilizing membrane proteins on a support. In fact, they show that, if appropriately chemically derived (in this case, by biotin grafting, but a number of other derivation methods can be used), the amphipols can be easily used, without undue development, for immobilizing any membrane protein at the surface of a solid support.

Furthermore, the results obtained show that the proteins thus immobilized can be used for studying interactions with ligands (in the present case, for detecting circulating antibodies). The products according to the invention comprising a support and one or more membrane proteins attached to the surface thereof can thus be used for detecting the presence or absence in a biological specimen of a ligand of an immobilized membrane protein at the support surface, and different types of applications are then possible, like for example:

detecting circulating antibodies raised against a membrane antigen, as shown herein, or screening a compound bank for pharmacologically valuable membrane receptor ligands, for identifying agonists or antagonists of said receptor.

Furthermore, the results obtained show that the proteins thus immobilized can be used for providing enzyme reactors: the products according to the invention comprising a support (beads, membranes, fibers, nanotubes and the like) and one or more membrane proteins attached to the surface thereof can in fact be used for exposing to said proteins products circulating in the solution, on which said proteins will have an enzymatic action.

Example 2

Membrane Protein Immobilization at the Surface of Streptavidin-Carrying Magnetic Beads by Means of a Biotinylated Amphipol The inventors tested bacteriorhodopsin (BR) immobilization on magnetic beads functionalized by binding to streptavidin (SA beads).

BR was complexed with biotinylated amphipol (BAPol) according to the following method: a BR solution in octyl thioglucoside detergent (OTG) contains 1.1 g/l protein, 18 mM OTG. 17 µl of a 100 g/l BAPol solution in water are added to 300 µl of protein solution (i.e. 5 g of BAPol per g of BR).

After incubation for 15 min, 80 mg of Bio-beads are added and incubation is left to proceed under stirring for 3 hr at 4° C. (adsorption of OTG) followed by recovery of the solution and removal of the Bio-beads.

100 mg of SA beads were washed 3 times in NaCl-HEPES buffer (150 mM NaCl, 10 mM HEPES at pH 7.4), then excess liquid was removed; the protein solution was diluted to 13 mg/L in NaCl-HEPES buffer.

At time zero, the protein solution is added to the beads and the mixture is stirred on a Vortex at 4° C. The sample is recovered 1 hr and 45 min. later. The beads are separated by means of a magnet, and the supernatant is analyzed. BR immobilization is monitored by measuring the optical density of the solution before and after incubation in the presence of beads.

Figure 9:
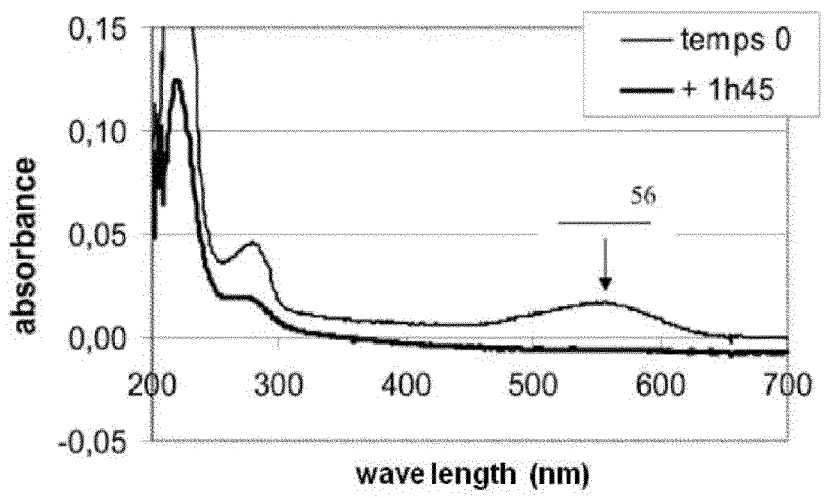
FIG. 9. Immobilization of bacteriorhodopsin membrane protein (BR) on streptavidin-carrying magnetic beads. The absorbance (or optical density) of the solution of BR protein complexed with biotinylated amphipol (BAPol) at time 0 (prior to mixing with the beads) and after incubation for 1 hr and 45 min. with streptavidin-carrying beads is measured versus wavelength. The analysis is carried out for the presence of a peak characteristic of BR protein at 560 nm.

The results are illustrated in FIG. 9 and show that the peak characteristic of BR at 560 nm has disappeared after the incubation, which indicates the binding of BR to the magnetic SA beads.

These results demonstrate that it is also possible to immobilize membrane proteins to beads.

Example 3

Synthesis of a Polyhistidine-Labelled Amphipol (HISTAPol)

The structure of biotinylated amphipol (BAPol) is described in FIG. 3.

The method for synthesizing polyhistidine-labelled amphipol (HISTAPol) is derived from the method for non-functionalized amphipols (7, 16-17) and comprises three steps.

The first step comprises forming amide bonds with the carboxylic acid functionalities of a low molecular weight polyacrylic acid and appropriately selected alkylamines, such as isopropylamine and octylamine.

The second step involves work-up of a histidine hexamer. This synthesis is carried out on a solid support using an automated technique involving double coupling of the selectively protected monomer.

Figure 10:
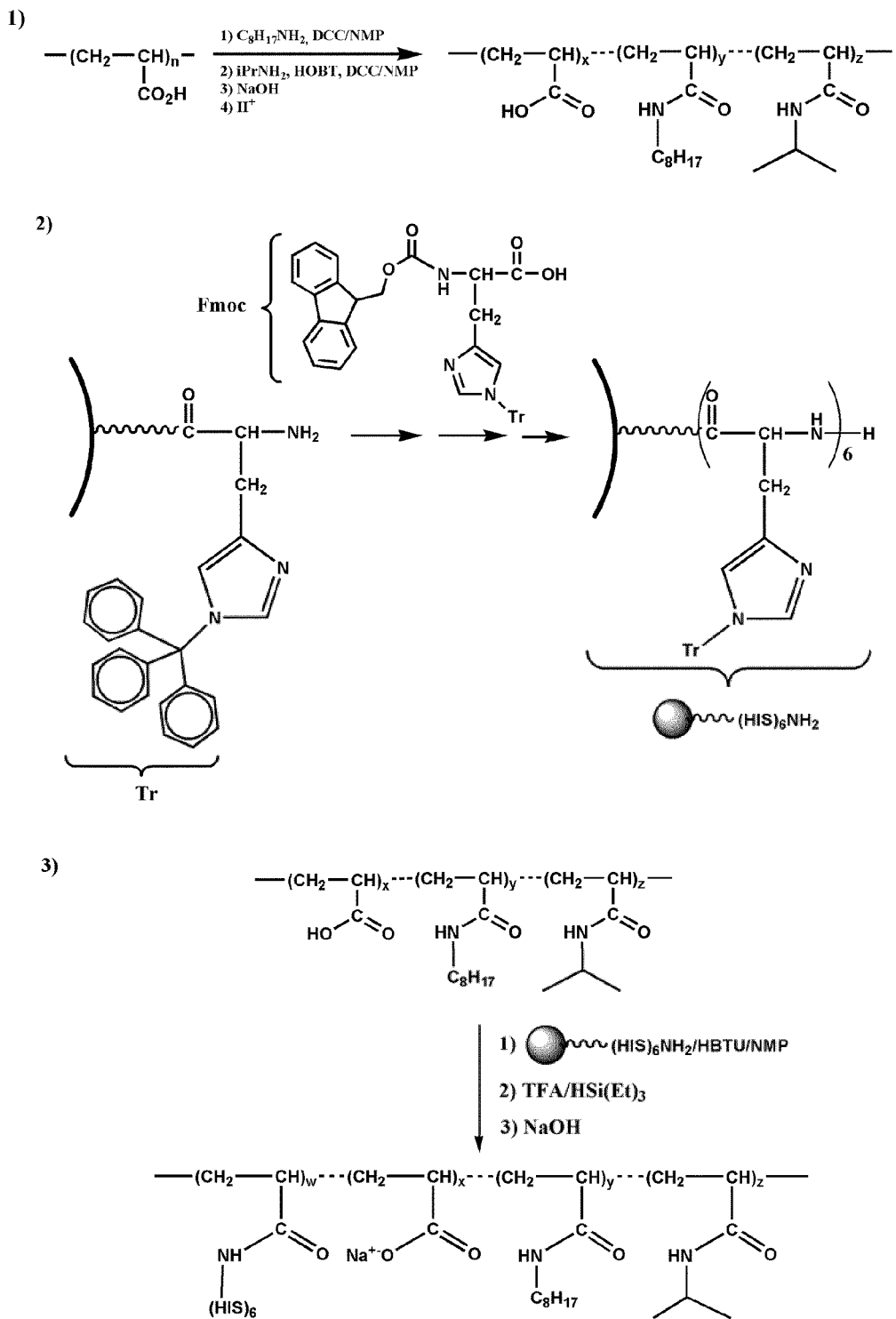
FIG. 10. Synthesis diagram of a polyhistidine-labelled amphipol. DCC: dicyclohexyl carbodiimide, NMP: N-methylpyrrolidinone, HOBT: N-hydroxybenzotriazole, iPr: isopropyl, FMOC: 9-fluorenylmethoxycarbonyl, HIS: histidine, TFA: trifluoroacetic acid, HBTU: O-Benzotriazol-N,N,N', N'-tetramethyl-uronium-hexafluoro-phosphate, Tr: trityl.

The last step comprises condensing the peptide N-termination onto the acid functionalities of the amphipol resulting from the first step of the synthesis. The peptide is used while still protected on its side chains and bound to the solid support. The amounts of amphipols and peptide used are calculated so as not to be higher than 2% of poly(histidine) label grafting. After deprotection and cleavage of the peptide from the solid support, the HISTAPol is conventionally purified. The synthesis is described in FIG. 10.

Such a synthesis can be carried out with another type of amphipol or amphiphilic molecule. Furthermore, other synthesis processes may also be used for synthetizing amphiphilic molecules, and in particular amphipols carrying a poly(histidine) label.

Such functionalized amphipols may be used to attach membrane proteins complexed with these amphipols to supports carrying Ni-NTA groups.

Bibliography

1. Giess F. et al. (2004). The protein-tethered lipid bilayer: a novel mimic of the biological membrane. *Biophys. J.* 87(5), 3213-20.
2. Pal P. et al. (2005). A novel immobilization method for single protein spFRER studies. Biophys. J. 89(2), Lll-3
3. Hoffman T. L. et al. (2000) A biosensor assay for studying ligand-membrane receptor interactions: binding of antibodies and HIV-1 Env to chemokine receptors. PNAS, 97, 11215-11220.
4. Minic J. et al. (2005). Immobilization of native membrane-bound rhodopsin on biosensor surfaces. Biochim. Biophys. Acta, 1724(3), 324-32
5. Cooper M. A (2002) Optical biosensor in drug discovery. Nat. rev. Drug Discov. 1, 515-528
6. EP0946875
7. Tribet, C, Audebert, R. & Popot, J.-L. (1996). Amphipols: polymers that keep membrane proteins soluble in aqueous solutions. Proc. Natl. Acad. Sci. USA 93, 15047-15050.
8. Popot, J.-L., Berry, E. A., Charvolin, D., Creuzenet, C, Ebel, C, Engelman, D. M., Flötenmeyer, M., Giusti, F., Gohon, Y., Hervé, P., Hong, Q., Lakey, J. H., Leonard, K., Shuman, H. A., Timmins, P., Warschawski, D. E., Zito, F., Zoonens, M., Pucci, B. & Tribet, C. (2003). Amphipols: polymeric surfactants for membrane biology research. Cell. Mol. Life Sci. 60, 1559-1574.
9. Zoonens, M., Catoire, L. J., Giusti, F. & Popot, J.-L. (2005). NMR study of a membrane protein in detergent-free aqueous solution. Proc. Natl. Acad. Sci. USA 102, 8893-8898.
10. Picard, M., Dahmane, T., Garrigos, M., Gauron, C, Giusti, F., le Maire, M., Popot, J.-L. & Champeil, P. (2006). Protective and inhibitory effects of various types of amphipols on the $Ca^{2+}$-ATPase from sarcoplasmic reticulum: a comparative study. Biochemistry 45, 1861-1869.
11. Nagy, J. K., Kuhn Hoffmann, A., Keyes, M. H., Gray, D. N., Oxenoid, K. & Sanders, C. R. (2001). Use of amphipathic polymers to deliver a membrane protein to lipid bilayers. FEBS Lett. 501, 115-120.
12. Q. Xu, K. S. Lam, Protein and Chemical Microarrays: Powerful Tools for Proteomics, J. Biomed. Biotechnol, 2003, 257, 2003.
13. M. N. Yousaf, M. Mrksich, Diels-Alder Reaction for the Selective Immobilization of Protein to Electroactive Self-Assembled Monolayers, J. Am. Chem. Soc, 121, 4286, 1999.
14. N. K. Devaraj, G. P. Miller, W. Ebina, B. Kakaradov, J. P. Collman, E. T. Kool, C. E. D. Chidsey, Chemoselective Covalent Coupling of Oligonucleotide Probes to Self-Assembled Monolayers, J. Am. Chem. Soc, 127, 6800, 2005.
15. I. Taniguchi, A. M. Mayes, E. W. L. Chan, L. G. Griffith, A Chemoselective Approach to Grafting Biodegradable Polyesters, Macromolecules, 38, 216-219, 2005.
16. Gohon, Y., Pavlov, G., Timmins, P., Tribet, C, Popot, J.-L. & Ebel, C. (2004). Partial specific volume and solvent interactions of amphipol A8-35. Anal. Biochem. 334, 318-334.
17. Gohon, Y., Giusti, F., Prata, C, Charvolin, D., Timmins, P., Ebel, C, Tribet, C. & Popot, J.-L. (2006). Well-defined nanoparticles formed by hydrophobic assembly of a short and polydisperse random terpolymer, amphipol A8-35. Langmuir 22, 1281-1290.

The invention claimed is:

1. A product comprising a support and at least one membrane protein attached to the surface thereof,
   wherein said membrane protein is attached to said support through an amphiphilic molecule with which said membrane protein is complexed, the binding to the support being done through the amphiphilic molecule, wherein the amphiphilic molecule is a vinyl polymer of the formula (I):

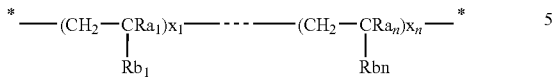

wherein:
$Ra_1$ to $Ra_n$ are the same or different, and represent a hydrogen atom, or a methyl radical;
$Rb_1$ to $Rb_n$ are different and selected from:
  a) a hydrophilic group selected from:
    i) a carboxylate radical —COO⁻M⁺, a sulfonate radical —SO$_3^-$M⁺, or a phosphonate radical —PO$_3^-$M⁺, wherein M⁺ is a cationic counter-ion;
    ii) a ($C_1$-$C_5$) alkylcarboxylate radical, a ($C_1$-$C_5$) alkylsulfonate radical, or a ($C_1$-$C_5$) alkylphosphonate radical;
    iii) a phenylsulfonate;
    iv) CONRc1Rc2, wherein Rc1 and Rc2, which may be the same or different, represent a (—C(CH$_2$ORd1)(CH$_2$ORd2)(CH$_2$ORd3)) radical, wherein Rd1, Rd2 and Rd3 represent independently a hydrogen atom, a sugar moiety, a polyoxyalkylene containing from 4 to 10 alkylene oxide units, a zwitterionic radical, a primary, secondary or tertiary hydroxyalkyl —(CH$_2$)mOH, wherein m is within the range of 1 to 4, a ($C_1$-$C_5$) alkylcarboxylate radical, a ($C_1$-$C_5$) alkylsulfonate radical, a ($C_1$-$C_5$) alkylphosphonate radical, or a sugar moiety;
    v) COORe, wherein Re represents a sugar moiety, a primary, secondary or tertiary hydroxyalkyl —(CH$_2$)mOH, wherein m is within the range of 1 to 4, a polyoxyalkylene having 4 to 10 alkylene oxide units, a (CH$_2$)t-NRf1Rf2 radical, wherein t is an integer from 1 to 5, and Rf1, Rf2, which may be the same or different, represent a hydrogen atom or a ($C_1$-$C_4$) alkyl radical;
    vi) a hydroxyl group;
    vii) a primary, secondary or tertiary hydroxyalkyl —(CH$_2$)mOH, wherein m is within the range of 1 to 4;
    viii) a primary, secondary, tertiary amine;
    ix) a quaternary ammonium;
    x) N-formamide or N-alkylformamide;
    xi) N-acetamide or N-alkylacetamide;
    xii) N-pyrrolidonyl;
    xiii) CONRg1Rg2, wherein Rg1 and Rg2, which may be the same or different, are a hydrogen atom, a sugar moiety, a polyoxyalkylene containing from 4 to 10 alkylene oxide units, a zwitterionic radical, a primary, secondary or tertiary hydroxyalkyl —(CH$_2$)mOH, wherein m is within the range of 1 to 4; and
    xiv) COORh or CONRkRl, wherein Rh represents a ($C_1$-$C_5$) alkyl radical, an alkylsulfonate, or has one of the meanings given for Re or Rg1, provided that it is not a hydrogen atom, and Rk and Rl have independently one of the meanings given for Rh, and additionally one of them can represent a hydrogen atom;
  b) a hydrophobic group selected from:
    i) a hydrogen atom;
    ii) a halogen atom;
    iii) a —CONH(—C(CH$_2$Orm1)(CH$_2$Orm2)(CH$_2$Orm3)) radical, wherein Rm1, Rm2, Rm3 are independently a linear or branched alkyl, alkenyl or alkynyl having from 3 to 50 carbon atoms, an alkylcarbamoyl (O=C—NH—Rn) or an acyl (O=C—Ro), where Rn and Ro are linear or branched alkyl, alkenyl or alkynyl radicals having from 3 to 50 carbon atoms;
    iv) COORp, CORp, COSRp, C—NH—Rp or CONRq1Rq2, wherein Rp is a linear or branched and/or cyclic alkyl, alkynyl or alkenyl radical containing from 3 to 50 carbon atoms, and Rq1 and Rq2, which may be the same or different, have one of the meanings given for Rp, and further either one of them can represent a hydrogen atom; and
    v) a —Rr, —ORr, or —SRr radical wherein Rr represents a linear or branched and/or cyclic alkyl, alkenyl or alkynyl group containing from 3 to 50 carbon atoms; and
  c) an amphiphilic group selected from:
    i) an alkyl radical —(CH$_2$)m-Rs, wherein m is between 6 and 20, and Rs is a hydrophilic group chosen from carboxylate, sulfonate, phosphonate, sulfate, phosphate, zwitterion, ammonium, poly(oxyethylene), and sugar,
    ii) a poly(oxyethylene)-O-alkyl radical (—(CH$_2$CH$_2$O)m-Rt) wherein Rt is a linear, branched or cyclic alkyl, alkenyl, alkynyl radical with 6 to 20 carbon atoms;
    iii) a COORu, CORu, COSRu, CONRvRw radical, wherein Ru is a poly(oxyethylene)-O-alkyl radical (—(CH$_2$CH$_2$O)m-Rt) and wherein Rt is a linear, branched or cyclic alkyl, alkenyl, alkynyl radical with 6 to 20 carbon atoms, a glycosylalkyl radical, wherein Rv may be a hydrogen atom or has one of the meanings given for Ru, wherein Rw has one of the meanings given for Ru; and
    iv) a —CONH(—C(CH$_2$ORx1)(CH$_2$ORx2)(CH$_2$ORx3 ))radical, wherein Rx1, Rx2, Rx3 are such that one or two of these groups have one of the meanings given for Rm1, Rm2, Rm3 and one or two of these groups are different from a hydrogen atom and have one of the meanings given for Rd1, Rd2, Rd3, and Ru; or Rx1, Rx2, Rx3 are the same or different, and are such that at least one of the groups is different from a hydrogen atom and has one of the meanings given for Ru;
n is an integer equal to or greater than 2;
$x_1$ to $x_n$ represent, respectively, the percentages of the units, $$\left(\sum_{i=1}^{n} x_i = 100\%\right),$$

wherein the ratio of the total percentage of groups wherein $Rb_i$ is a hydrophobic or amphiphilic group to the total percentage of groups wherein $Rb_i$ is a hydrophilic group $$\left(\sum_{hydrophobic\ Rb_i} x_i + \sum_{amphiphilic\ Rb_j} x_j\right) \Big/ \sum_{hydrophilic\ Rb_k} x_k$$

is between 0.25 and 2.5; and the average molecular weight is between 500 and 100,000, wherein the binding of the amphiphilic molecule to the support is mediated by a specific receptor-ligand binding between at least one functional group in the amphiphilic molecule and at least one functional group at the support surface, or a covalent bond between at least one reactive functional group in the amphiphilic molecule and at least one reactive functional group at the support surface, and wherein the polymer of formula (1) further comprises a percentage of between 0 and 4% of a monomer of the formula

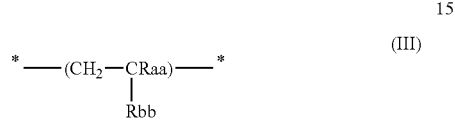
(III)

wherein:

Raa is a hydrogen atom or a methyl radical;

Rbb represents a COORcc, or —COSRcc or —CORcc or CONRccRdd group;

Rcc represents the functional group in the amphiphilic molecule providing a first half of a receptor-ligand pair or a first half of a chemical reactive pair; and Rdd represents a ($C_1$-$C_5$) alkyl radical, an alkylsulfonate, a hydrogen atom, a sugar moiety, a primary, secondary or tertiary hydroxyalkyl —($CH_2$)mOH, where m is within the range of 1 to 4, a polyoxyalkylene having 4 to 10 alkylene oxide units, a zwitterionic radical, a ($CH_2$)t-NRf1Rf2 radical, where t is an integer from 1 to 5, Rf1, Rf2 are the same or different, and represent a hydrogen atom or a ($C_1$-$C_4$) alkyl radical.

2. The product according to claim 1 wherein n is 3 and the vinyl polymer has the formula (II):

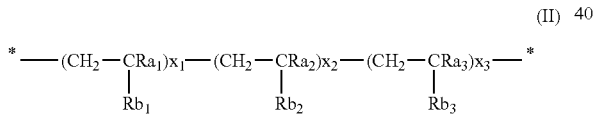
(II)

wherein:

$Ra_1$, $Ra_2$ and $Ra_3$ are the same or different, and represent a hydrogen atom, or a methyl radical;

$Rb_1$ is a hydrophilic group chosen from:
a) a carboxylate radical —$COO^-M^+$, a sulfonate radical —$SO_3^-M^+$, or a phosphonate radical —$PO_3^-M^+$, wherein $M^+$ is a cationic counter-ion;
b) a ($C_1$-$C_5$) alkylcarboxylate radical, a ($C_1$-$C_5$) alkylsulfonate radical, or a ($C_1$-$C_5$) alkylphosphonate radical;
c) a phenylsulfonate; and
d) CONRc1Rc2, wherein Rc1 and Rc2, which may be the same or different, represent a (—C($CH_2$ORd1)($CH_2$ORd2)($CH_2$ORd3)) radical, wherein Rd1, Rd2 and Rd3 represent independently a hydrogen atom, a sugar moiety, a polyoxyalkylene containing from 4 to 10 alkylene oxide units, a zwitterionic radical, a primary secondary or tertiary hydroxyalkyl —($CH_2$) mOH, wherein m is within the range of 1 to 4, a ($C_1$-$C_5$) alkylcarboxylate radical, a ($C_1$-$C_5$) alkylsulfonate radical, a ($C_1$-$C_5$) alkylphosphonate radical, or a sugar moiety;

$Rb_2$ is chosen from:
a) a hydrophobic group chosen from:
i) a hydrogen atom;
ii) a halogen atom;
iii) a —CONH(—C($CH_2$Orm1)($CH_2$ORm2)($CH_2$ORm3)) radical, wherein Rm1, Rm2, Rm3 are independently a linear or branched alkyl, alkenyl or alkynyl comprising from 3 to 50 carbon atoms, an alkylcarbamoyl (O=C—NH—Rn) or an acyl (O=C—Ro), wherein Rn and Ro are linear or branched alkyl, alkenyl or alkynyl radicals having from 3 to 50 carbon atoms;
iv) COORp, CORp, CSRp, C—NH—Rp or CONRq1Rq2, wherein Rp is a linear or branched and/or cyclic alkyl, alkynyl or alkenyl radical containing from 3 to 50 carbon atoms, and Rq1 and Rq2, which may be the same or different, have one of the meanings given for Rp, and further either one of them can represent a hydrogen atom; and
v) a —Rr, —ORr, or —SRr radical wherein Rr represents a linear or branched and/or cyclic alkyl, alkenyl or alkynyl group containing from 3 to 50 carbon atoms; or
b) an amphiphilic group chosen from:
i) an alkyl radical —($CH_2$)m-Rs, wherein m is between 6 and 20, Rs is a hydrophilic chosen from carboxylate, sulfonate, phosphonate, sulfate, phosphate, zwitterion, ammonium, poly(oxyethylene), and sugar;
ii) a poly(oxyethylene)-O-alkyl radical (—($CH_2CH_2$O)m-Rt) wherein Rt is a linear, branched or cyclic alkyl, alkenyl, alkynyl radical with 6 to 20 carbon atoms;
iii) a COORu, CORu, COSRu, CONRvRw radical, wherein Ru is a poly(oxyethylene)-O-alkyl radical (—($CH_2CH_2$O)m-Rt) and wherein Rt is a linear, branched or cyclic alkyl, alkenyl, alkynyl radical with 6 to 20 carbon atoms, a glycosylalkyl radical, wherein Rv may be a hydrogen atom or has one of the meanings given for Ru, wherein Rw has one of the meanings given for Ru; and
iv) a —CONH(—C($CH_2$ORx1)($CH_2$ORx2)($CH_2$ORx3)) radical, wherein Rx1, Rx2, Rx3 are such that one or two of these groups have one of the meanings given for Rm1, Rm2, Rm3, and one or two of these groups are different from a hydrogen atom and have one of the meanings given for Rd1, Rd2, Rd3, Ru; or Rx1, Rx2, Rx3 are the same or different, and are such that at least one of the groups is different from a hydrogen atom and has one of the meanings given for Ru;

$Rb_3$ is a hydrophilic group chosen from:
a) COORe, wherein Re represents a sugar moiety, a primary, secondary or tertiary hydroxyalkyl —($CH_2$) mOH, wherein m is within the range of 1 to 4, a polyoxyalkylene having 4 to 10 alkylene oxide units, a ($CH_2$)t-NRf1Rf2 radical, where t is an integer from 1 to 5, and Rf1, Rf2, which may be the same or different, represent a hydrogen atom or a ($C_1$-$C_4$) alkyl radical;
b) a hydroxyl group;
c) a primary, secondary or tertiary hydroxyalkyl —($CH_2$)mOH, wherein m is within the range of 1 to 4;
d) a primary, secondary, tertiary amine;
e) a quaternary ammonium;
f) N-formamide or N-alkylformamide;
g) N-acetamide or N-alkylacetamide;

h) N-pyrrolidonyl;
i) CONRg1Rg2, wherein Rg1 and Rg2, which may be the same or different, are a hydrogen atom, a sugar moiety, a polyoxyalkylene containing from 4 to 10 alkylene oxide units, a zwitterionic radical, a primary, secondary or tertiary hydroxyalkyl —$(CH_2)mOH$, wherein m is within the range of 1 to 4 (R3),
j) COORh or CONRkRl, wherein Rh represents a ($C_1$-$C_5$) alkyl radical, an alkylsulfonate, or has one of the meanings given for Re or Rg1, provided that it is not a hydrogen atom, and Rk, Rl have independently one of the meanings given for Rh, and additionally one of them can represent a hydrogen atom;
x1, x2, x3 represent the percentages of the units, respectively, wherein:
x1 is between 20 and 90%;
x2 is between 10 and 80%;
x3 is between 0 and 60%; and
$x_2/x_1+x_3$ is between 0.25 and 2.5; and
wherein the average molecular weight is between 500 and 100,000.

3. The product according to claim 2 wherein:
$Ra_1$, $Ra_2$ and $Ra_3$ are the same or different, and represent a hydrogen atom or a methyl radical;
$Rb_1$ represents $COO^-M^+$, wherein $M^+$ is a cationic counter-ion;
$Rb_2$ represents CONRq1Rq2, wherein Rq1 and Rq2 represent independently a linear or branched and/or cyclic alkyl, alkynyl or alkenyl radical containing from 3 to 50 carbon atoms, and further either one of them can represent a hydrogen atom;
$Rb_3$ represents CONRkRl, wherein Rk and Rl represent independently a ($C_1$-$C_5$) alkyl radical, an alkylsulfonate, a sugar moiety, a primary, secondary or tertiary hydroxyalkyl —$(CH_2)mOH$, wherein m is within the range of 1 to 4, a polyoxyalkylene having 4 to 10 alkylene oxide units, a zwitterionic radical, a $(CH_2)t-NRf1Rf2$ radical, wherein t is an integer from 1 to 5, Rf1, Rf2 are the same or different, and represent a hydrogen atom or a ($C_1$-$C_4$) alkyl radical, and further either one of Rk and Rl can represent a hydrogen atom.

4. The product according to claim 1 wherein the support is a solid support.

5. The product according to claim 4 wherein the support is chosen from a chip, a bead, a membrane, a fiber, a nanotube, and a soluble macromolecule or particle chosen from a polymer, a dendrimer, a vesicle, and a micelle.

6. The product according to claim 1 wherein the receptor-ligand pair (functional group in the amphiphilic molecule / functional group attached to the support) is chosen from the following pairs: (biotin/avidin), (glutathion/glutathion S-transferase, glutathion-binding proteins, or fusion proteins including glutathion S-transferase), (calmoduline/ATPase, protein kinase, phosphodiesterase, or neurotransmitter), (L-arginine or p-aminobenzamidine/serine protease), (L-lysine/plasminogen (and activator) or rRNA), (AMP, ADP, or ATP/Cofactor enzyme), (lectin/glucanated protein, glucolipid, or polysaccharide), (heparin/growth and coagulation factor, steroid receptor, endonuclease, lipoprotein, or lipase), or (Cibacron blue®/NAD or NADP cofactor enzymes, albumin, coagulation factor, or interferon), (antigen/antibody), (hapten/antibody), (antibody/antigen), (antibody/hapten), (nitrilotriacetic acid (NTA)/transition metal), (EDTA/transition metal), (phenylboronic acid (APB)/salicyl-hydrox-amic acid (ASH)), and (oligonucleotide/complementary oligonucleotide), and the corresponding reversed pairs.

7. The product according to claim 1 wherein the chemical reactive pair (reactive functional group in the amphiphilic molecule/reactive functional group attached to the support) is selected from the following pairs: (cyclopentadienyl group / quinone derivative), (alkynyl group/azide group), (alkoxylamine group/carbonyl group), and (carbonyl group/alkoxylamine group).

8. The product according to claim 1 wherein said at least one membrane protein is chosen from an antigen, an antibody, an enzyme, a cell receptor, an ion channel, and a membrane protein of viral, bacterial, or eukaryotic origin.

9. A process for preparing a product according to claim 1 comprising:
providing at least one membrane protein, a support, and an amphiphilic molecule according to claim 1;
forming a complex between the amphiphilic molecule and the membrane protein; and
attaching the amphiphilic molecule of the complex to the support via a hydrophobic bond, an ionic bond, a specific receptor-ligand binding between at least one functional group in the amphiphilic molecule and at least one functional group at the support surface, or a covalent bond between at least one reactive functional group in the amphiphilic molecule and at least one reactive functional group at the support surface.

10. A method for detecting the presence or absence in a biological specimen of a ligand of at least one membrane protein comprising preparation of a product according to claim 1 with said membrane protein and contacting said product with said biological specimen.

11. The method according to claim 10 wherein said at least one membrane protein is a membrane antigen of a pathogenic agent, said biological specimen is a serum sample, and said ligand to be detected is an antibody raised against said antigen.

12. A method for screening a bank of compounds for ligands of at least one membrane protein, comprising preparation,of a product according to claim 1 with said membrane protein and contacting said product with said bank of compounds.

13. A method for transforming an enzyme substrate under controlled conditions, comprising preparation of a product according to claim 1 with said membrane protein which is an enzyme and contacting said enzyme substrate.

14. A process for assaying a membrane protein in a sample, comprising:
a) solubilizing a membrane protein in a detergent;
b) preparing a product according to claim 1 by:
    i) complexing the membrane protein with an amphiphilic molecule and removing the detergent; and
    ii) immobilizing the membrane protein onto a support through the amphiphilic molecule,
c) extensively washing, and adding a protease for generating protein fragments of the membrane protein, wherein the transmembrane domain remains complexed with the amphiphilic molecule attached to the support; and
d) removing the support to which the transmembrane domain still complexed with the amphiphilic molecule remains bound, and analyzing the protein fragments by mass spectrometry.

* * * * *